(12) United States Patent
Schindler et al.

(10) Patent No.: US 7,326,789 B2
(45) Date of Patent: Feb. 5, 2008

(54) SULFUR SUBSTITUTED SULFONYLAMINOCARBOXYLIC ACID N-ARYLAMIDES, THEIR PREPARATION, THEIR USE AND PHARMACEUTICAL PREPARATIONS COMPRISING THEM

(75) Inventors: Ursula Schindler, Bad Soden (DE); Karl Schönafinger, Alzenau (DE); Hartmut Strobel, Liederbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 577 days.

(21) Appl. No.: 10/816,143

(22) Filed: Apr. 2, 2004

(65) Prior Publication Data

US 2004/0186145 A1  Sep. 23, 2004

Related U.S. Application Data

(62) Division of application No. 09/994,739, filed on Nov. 28, 2001, now Pat. No. 6,881,735, which is a division of application No. 09/349,933, filed on Jul. 8, 1999, now Pat. No. 6,335,334.

(30) Foreign Application Priority Data

Jul. 8, 1998  (DE) ............................... 198 30 430
Jan. 27, 1999  (DE) ............................... 199 03 126

(51) Int. Cl.
*C07D 215/36*  (2006.01)
*A61K 31/47*  (2006.01)

(52) U.S. Cl. .............. 546/172; 546/293; 546/548; 546/312.1; 546/243; 546/544; 546/405

(58) Field of Classification Search ............... 546/172, 546/293; 548/312.1, 243; 544/405
See application file for complete search history.

(56) References Cited

U.S. PATENT DOCUMENTS

| 6,015,822 | A | 1/2000 | Brendel et al. | |
|---|---|---|---|---|
| 6,087,399 | A | 7/2000 | Gerlach et al. | |
| 6,139,574 | A | 10/2000 | Vacanti et al. | |
| 6,150,356 | A | 11/2000 | Lloyd et al. | 514/218 |
| 6,511,977 | B1 | 1/2003 | Lloyd et al. | 514/233.8 |
| 6,548,547 | B1 | 4/2003 | Schindler et al. | 514/604 |

FOREIGN PATENT DOCUMENTS

| DE | 197 44 027 A1 | 4/1999 |
|---|---|---|
| EP | 876526 | 9/1961 |
| EP | 0 908 456 A1 | 4/1999 |
| EP | 1 614 678 A3 | 1/2006 |
| FR | 2 201 083 | 4/1974 |
| GB | 876526 | 9/1961 |
| HU | P9800277 A | 6/1999 |
| HU | P9802034 A | 3/2000 |
| HU | P9802590 A | 4/2000 |
| HU | P0001442 A | 11/2001 |
| JP | 04285955 A | 10/1992 |
| JP | 05027380 A | 2/1993 |
| JP | 07056293 A | 3/1995 |
| JP | 09043786 A | 2/1997 |
| WO | 96/31492 | 10/1996 |
| WO | WO 96/31492 | 10/1996 |
| WO | WO 98/49162 | 11/1998 |

OTHER PUBLICATIONS

International Search Report for PCT/EP9904426 (WO0002851).
English Language Abstract of JP 07056293 A, Mar. 3, 1995.
English Language Abstract of JP 09043786 A, Jul. 1995.
English Language Abstract of JP 05027380 A, Mar. 1991.
English Language Abstract of JP 04285955 A, Mar. 1991.
English Language Abstract of HU P9800277 A, Jul. 1995.
English Language Abstract of HU P9802034 A, Jul. 1995.
English Language Abstract of HU P9802590 A, Mar. 1991.
Alexander Mülsch, et al., "Purification of Heme-Containing Soluble Guanylyl Cyclase," *Methods In Enzymology*, vol. 195, pp. 377-383, 1991.

(Continued)

Primary Examiner—James O. Wilson
Assistant Examiner—Paul V. Ward
(74) Attorney, Agent, or Firm—Finnegan, Henderson, Farabow, Garrett and Dunner, L.L.P.

(57) ABSTRACT

The present invention relates to compounds of the formula I

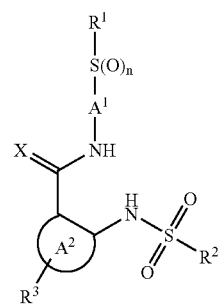

wherein $A^1$, $A^2$, $R^1$, $R^2$, $R^3$, X and n are as defined in the claims, which are valuable pharmaceutically active compounds for the therapy and prophylaxis of diseases, for example of cardiovascular diseases such as hypertension, angina pectoris, cardiac insufficiency, thromboses or atherosclerosis. The compounds of the formula I are capable of modulating the body's production of cyclic guanosine monophosphate (cGMP) and are generally suitable for the therapy and prophylaxis of diseases which are associated with a disturbed cGMP balance. The invention furthermore relates to processes for preparing compounds of the formula I, to their use for the therapy and prophylaxis of the abovementioned diseases and for preparing pharmaceuticals for this purpose, and to pharmaceutical preparations which comprise compounds of the formula I.

10 Claims, No Drawings

OTHER PUBLICATIONS

Hirano et al., "Silver Halide Photographic Material," *Chemical Abstracts*, 119:105757f:726, 1993.

Nagaoka et al., "Color Photographic Material With Good Sharpness and Low Minimum Density," *Chemical Abstracts*, 120:41858a:807, 1994.

Fukagawa et al., "Direct Positive Color Photographic Material For Color Image Formation and Color Proof," *Chemical Abstracts*, 123:70224h:1043, 1995.

Matsumoto et al., "Silver Halide Color Photographic Material With Excellent Color Reproduction, Sharpness and Storage Stability," *Chemical Abstracts*, 126:257007u:1075, 1997.

Vesely, D.L., "B complex vitamins activate rat guanylate cyclase and increase cyclic GMP levels," *European Journal of Clinical Investigation*, 1985, 15:258-262.

Vesely, D.L., "Phencyclidine Stimulates Guanylate Cyclase Activity," *Biochemical and Biophysical Research Communications*, 1979, 88:4:1244-1248.

Ignarro, L.J., "Regulation of Cytosolic Guanylyl Cyclase by Porphyrins and Metalloporphyrins," *Advances in Pharmacology*, 1994, 26:35-65.

Pettibone, D.J., et al., "A Structurally Novel Stimulator of Guanylate Cyclase With Long-Lasting Hypotensive Activity In The Dog," *European Journal of Pharmacology*, 1985, 116:307-312.

Yu, S.M., et al., "Vasorelaxant effect of isoliquiritigenin, a novel soluble guanylate cyclase activator, in rat aorta," *British Journal of Pharmacology*, 1995, 114:1587-1594.

Ko, F.N., et al., "YC-1, a Novel Activator of Platelet Guanylate Cyclase," *Blood*, 1994, 84:12:4226-4233.

Yu, S.M., et al., "Mechanism of anti-proliferation caused by YC-1, an indazole derivative, in cultured rat A10 vascular smooth-muscle cells," *Biochem. J.*, 1995, 306:787-792.

Wu, C.C., et al., "YC-1 inhibited human platelet aggregation through NO-independent activation of soluble guanylate cyclase," *British Journal of Pharmacology*, 1995, 116:1973-1978.

Konishiroku Photo Industry Co., *Chemical Abstracts*, vol. 102, abstract 140722, 1996.

Ikegami, *Chemical Abstracts*, vol. 122, abstract 92744, (1996).

Ooya, *Chemical Abstracts*, vol. 124:274354. (1996).

Lloyd et al., Chemical Abstracts, vol. 132: 207763, 2000.

Ferlux-Chemie S.A., Chemical Abstracts, vol. 82: 16861, 1975.

SULFUR SUBSTITUTED SULFONYLAMINOCARBOXYLIC ACID N-ARYLAMIDES, THEIR PREPARATION, THEIR USE AND PHARMACEUTICAL PREPARATIONS COMPRISING THEM

This is a division of application Ser. No. 09/994,739, filed Nov. 28, 2001 now U.S. Pat. No. 6,881,735, which is a division of application Ser. No. 09/349,933, filed Jul. 8, 1999, and issued on Jan. 1, 2002 as U.S. Pat. No. 6,335,334, which claims priority under 35 U.S.C. § 119 to German patent application No. 19830430.7 filed on Jul. 8, 1998, and No. 19903126.6 filed on Jan. 27, 1999; all four prior applications are incorporated herein by reference in their entirety.

The present invention relates to compounds of the formula I

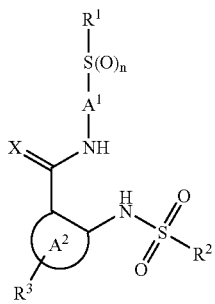

wherein $A^1$, $A^2$, $R^1$, $R^2$, $R^3$, X and n are as defined below, which are valuable pharmaceutically active compounds for the therapy and prophylaxis of diseases, for example for cardiovascular diseases such as hypertension, angina pectoris, cardiac insufficiency, thromboses or atherosclerosis. The compounds of the formula I are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of the formula I, to their use for the therapy and prophylaxis of the abovementioned diseases and for preparing pharmaceuticals for this purpose, and to pharmaceutical preparations which comprise compounds of the formula I.

cGMP is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is being discussed as activation mechanism of the activation by NO. The associated release of the histidine which is bound in the basal state to the iron converts the enzyme into the active conformation.

Active soluble guanylate cyclases are composed of an α and a β subunit each. Several subunit subtypes have been described which differ from one another with respect to sequence, tissue-specific distribution and expression in different development stages. The subtypes $α_1$ and $β_1$ are mainly expressed in brain and lung, while $β_2$ is found in particular in liver and kidney. The subtype $α_2$ was shown to be present in human fetal brain. The subunits referred to as $α_3$ and $β_3$ were isolated from human brain and are homologous to $α_1$ and $β_1$. More recent works indicate an $α_{2i}$ subunit which contains an insert in the catalytic domain. All subunits show great homologies in the region of the catalytic domain. The enzymes presumably contain one heme per heterodimer, which is bound via $β_1$-Cys-78 and/or $β_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has hitherto almost exclusively been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, *Eur. J. Clin. Invest.*, vol. 15,1985, p. 258; D. L. Vesely, *Biochem. Biophys. Res. Comm.*, vol. 88, 1979, p. 1244. A stimulation of heme-free guanylate cyclase by protoporphyrin IX was demonstrated by Ignarro et al., *Adv. Pharmacol.*, vol. 26, 1994, p. 35. Pettibone et al., *Eur. J. Pharmacol.*, vol. 116, 1985 p. 307, described an antihypertensive action of diphenyliodonium hexafluorophosphate and attributed this to a stimulation of sGC. According to Yu et al., *Brit. J. Pharmacol.*, vol. 114, 1995, p. 1587, isoliquiritigenin, which has a relaxing action on isolated rat aortas, also activates sGC. Ko et al., *Blood* vol. 84, 1994, p. 4226, Yu et al., *Biochem. J.* vol. 306, 1995, p. 787, and Wu et al., *Brit. J. Pharmacol.* vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). If isolated structural elements are considered then the N-aryl group in these known compounds corresponds to the group $R^1$—$S(O)_n$—$A^1$ in formula I in case $A^1$ denotes a 1,4-phenylene residue which in positions 2 and 5 carries hydroxy groups (or oxy substituents), and the number n is 0. British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths. Compounds covered by British patent publication No. 876,526 correspond to compounds of the formula I if simultaneously the ring $A^1$ which comprises the carbon atoms which carry the groups C(=X)—NH— and NH—$SO_2R^2$, together with the residues $R^3$, is a benzene ring which carries one to four halogen atoms from the series chlorine and bromine, $R^2$ is $(C_1-C_4)$-alkyl, X is oxygen and the group $R^1$—$S(O)_n$—$A^1$— is a phenylmercaptophenyl-residue (=phenylthiophenyl-) which is substituted by halogen and/or trifluoromethyl and which can also be substituted by methyl or $(C_1-C_4)$alkoxy, and the total number of halogen atoms and trifluoromethyl groups is greater than two. Pharmacological activities of these known 2-sulfonylaminobenzoic acid N-arylamides are not disclosed.

Surprisingly, it has now been found that the compounds of the present invention effect a strong activation of guanylate cyclase and are therefore suitable for the therapy and prophylaxis of disorders which are associated with a low cGMP level.

Thus, the present invention relates to compounds of the formula l:

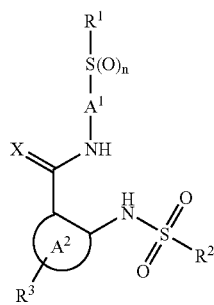

I wherein
$A^1$ is a divalent residue from the series phenylene, naphthylene and heteroarylene which can all be substituted by one or more identical or different substituents from the series halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, —NH—CHO, —NH—CO—$(C_1-C_5)$-alkyl, —CN, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl, CHO, —CO—$(C_1-C_5)$-alkyl, —$S(O)_n$—$(C_1-C_4)$-alkyl, —$S(O)_n$-phenyl and —$S(O)_n$-tolyl;

the ring $A^2$ which comprises the carbon atoms which carry the groups C(=X)—NH— and NH—$SO_2R^2$ is a benzene ring, a naphthalene ring, a saturated or partially unsaturated 3-membered to 7-membered carbocycle, a saturated or partially unsaturated or aromatic monocyclic 5-membered to 7-membered heterocycle which contains one or more ring heteroatoms from the series N, O and S, or a saturated or partially unsaturated or aromatic bicyclic 8-membered to 10-membered heterocycle which contains one or more ring heteroatoms from the series N, O and S;

$R^1$ is aryl, heterocyclyl or $(C_1-C_{18})$-alkyl which can be substituted by one or more identical or different residues $R^4$ or, if the number n in the group $R^1$—$S(O)_n$— is 2, $R^1$ can also be $NR^5R^6$ or, if the number n in the group $R^1$—$S(O)_n$— is 0, $R^1$ can also be —CN;

$R^2$ is aryl, heterocyclyl, $NR^5R^6$ or $(C_1-C_{10})$-alkyl which can be substituted by one or more identical or different residues $R^4$;

$R^3$ denotes one or more identical or different residues from the series hydrogen, halogen, $CF_3$, OH, —O—$(C_1-C_7)$-alkyl, —O—$(C_2-C_4)$-alkyl-O—$(C_1-C_7)$-alkyl, —O-aryl, $(C_1-C_2)$-alkylenedioxy, $NO_2$, —CN, $NR^7R^8$, —CO—$NR^7R^8$, —CO—OH, —CO—O—$(C_1-C_5)$-alkyl, heterocyclyl, —$S(O)_n$—$(C_1-C_5)$-alkyl and $(C_1-C_5)$-alkyl which can be substituted by one or more identical or different residues $R^4$;

$R^4$ is fluorine, OH, —O—$(C_1-C_{10})$-alkyl, —O—$(C_2-C_4)$-alkyl-O—$(C_1-C_7)$-alkyl, —O-aryl, —CN, $NR^7R^8$, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl or oxo;

$R^5$ is hydrogen, $(C_1-C_{10})$-alkyl which can be substituted by one or more identical or different substituents $R^4$ and/or by aryl, or is aryl, heterocyclyl, —CO—$NR^7R^8$, —CO-aryl or —CO—$(C_1-C_{10})$-alkyl wherein the alkyl residue can be substituted by one or more identical or different residues $R^4$;

$R^6$ independently of $R^5$ has one of the meanings indicated for $R^5$, or $R^5$ and $R^6$ together with the nitrogen atom to which they are bonded form a 5-membered to 8-membered saturated or partially unsaturated ring which in addition to the nitrogen atom which carries the groups $R^5$ and $R^6$ can contain one or more further ring heteroatoms from the series N, O and S and which can be substituted by one or more identical or different substituents from the series fluorine, $(C_1-C_5)$-alkyl, hydroxy-$(C_1-C_3)$-alkyl-, —$(C_1-C_3)$-alkyl-O—$(C_1-C_4)$-alkyl, aryl, $CF_3$, OH, —O—$(C_1-C_7)$-alkyl, —O-aryl, —O—$(C_2-C_4)$-alkyl-O—$(C_1-C_7)$-alkyl, $(C_2-C_3)$-alkylenedioxy, $NR^7R^8$, —CN, —CO—$NH_2$, —CO—NH—$(C_1-C_3)$-akyl, —CO—N$((C_1-C_3)$-alkyl$)_2$, —CO—OH, —CO—O—$(C_1-C_5)$-alkyl, CHO, —CO—$(C_1-C_5)$-alkyl, —$S(O)_n$—$(C_1-C_4)$-alkyl, —$S(O)_n$—N H$_2$, —$S(O)_n$—NH—$(C_1-C_3)$-alkyl, —$S(O)_n$—N$((C_1-C_3)$-alkyl$)_2$, oxo, —$(CH_2)_m$—$NH_2$, —$(CH_2)_m$—NH—$(C_1-C_4)$-alkyl and —$(CH_2)_m$—N$((C_1-C_4)$-alkyl$)_2$ where in the substituent —$(CH_2)_m$—N$((C_1-C_4)$-alkyl$)_2$ the two alkyl groups can be connected by a single bond and then together with the nitrogen atom carrying them form a 5-membered to 7-membered ring which besides that nitrogen atom and the carbon atoms can additionally contain an oxygen atom, a sulfur atom or a group $NR^5$ as ring member;

$R^7$ is hydrogen or $(C_1-C_7)$-alkyl which can be substituted by one or more identical or different substituents from the series OH, —O—$(C_1-C_5)$-alkyl, $NH_2$, —NH—$(C_1$-

$C_4$)-alkyl and —N(($C_1$-$C_4$)-alkyl)$_2$ where in the substituent N(($C_1$-$C_4$)-alkyl)$_2$ the two alkyl groups can be connected by a single bond and then together with the nitrogen atom carrying them form a 5-membered to 7-membered ring which besides that nitrogen atom and the carbon atoms can additionally contain an oxygen atom, a sulfur atom or a group NR$^5$ as ring member;

$R^8$ independently of $R^7$ has one of the meanings of $R^7$ or is —CO—($C_1$-$C_4$)-alkyl;

"aryl" is phenyl, naphthyl or heteroaryl which can all be substituted by one or more identical or different substituent from the series halogen, ($C_1$-$C_5$)-alkyl, phenyl, tolyl, $CF_3$, —O—$CF_3$, $NO_2$, OH, —O—($C_1$-$C_5$)-alkyl, —O—($C_2$-$C_4$)-alkyl-O—($C_1$-$C_3$)-alkyl, ($C_1$-$C_2$)-alkylenedioxy, $NH_2$, —NH—($C_1$-$C_3$)-alkyl, —N(($C_1$-$C_3$)-alkyl)$_2$, —NH—CHO, —NH—CO—($C_1$-$C_5$)-alkyl, —CN, —CO—$NH_2$, —CO—NH—($C_1$-$C_3$)-alkyl, —CO—N(($C_1$-$C_3$)-alkyl)$_2$, —CO—OH, —CO—O—($C_1$-$C_5$)-alkyl, heterocyclyl, CHO, —CO—($C_1$-$C_5$)-alkyl, —S(O)$_n$—($C_1$-$C_4$)-alkyl, —S(O)$_n$-phenyl and —S(O)$_n$-tolyl;

"heteroaryl" and "heteroarylene" are a residue of a monocyclic 5-membered or 6-membered aromatic heterocycle or of a bicyclic 8-membered to 10-membered aromatic heterocycle each of which contains one or more ring heteroatoms from the series N, O and S;

"heterocyclyl" is a residue of a monocyclic or polycyclic 5-membered to 11-membered saturated or partially unsaturated heterocycle which contains one or more ring heteroatoms from the series N, O and S and which can be substituted by one or more identical or different substituents from the series fluorine, ($C_1$-$C_5$)-alkyl, OH, —O—($C_1$-$C_5$)-alkyl, —O—($C_2$-$C_4$)-alkyl-O—($C_1$-$C_3$)-alkyl, $NH_2$, —NH—($C_1$-$C_3$)-alkyl, —N(($C_1$-$C_3$)-alkyl)$_2$, —CN, —CO—$NH_2$, —CO—NH—($C_1$-$C_3$)-alkyl, —CO—N(($C_1$-$C_3$)-alkyl)$_2$, —CO—OH and —CO—O—($C_1$-$C_5$)-alkyl;

n is 0, 1 or 2;

m is 2, 3 or 4;

X is O or NH or X is a nitrogen atom which via a single bond is attached to a ring carbon atom in the group $A^1$ which ring carbon atom is directly adjacent to the carbon atom in $A^1$ carrying the group —NH—C(=X)— so that the group —NH—C(=X)— together with the carbon atoms in $A^1$ carrying it forms an anellated imidazole ring;

in all their stereoisomeric forms and mixtures thereof in all ratios, and their physiologically acceptable salts;

where, however, the compound of formula I is excluded wherein simultaneously the ring $A^2$ which comprises the carbon atoms which carry the groups C(=X)—NH— and NH—$SO_2R^2$ is a benzene ring which is substituted in positions 3 and 5 by chlorine, $R^2$ is methyl, X is oxygen and $R^1$—S(O)$_n$-$A^1$— is a 5-chloro-2-(4-chlorophenylmercapto)-phenyl residue.

If groups or substituents can occur several times in the compounds of formula I such as, for example $R^3$, $R^4$, $R^5$, aryl, heterocyclyl, alkyl, or the numbers n and m, they can all independently of one another have the meanings indicated and can in each case be identical or different.

Alkyl residues can be straight-chain or branched. This also applies when they are part of other groups, for example in alkoxy groups, alkoxycarbonyl groups or amino groups, or when they are substituted. Examples of alkyl groups are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, the n-isomers of these residues, isopropyl, isobutyl, isopentyl, sec-butyl, tert-butyl, neopentyl, 3,3-dimethylbutyl. The term alkyl here also expressly includes unsaturated alkyl residues, i.e. alkyl residues which contain one or more double bonds and/or one or more triple bonds such as, for example, alkenyl residues and alkinyl residues. Of course, an unsaturated alkyl group contains at least two carbon atoms. Specific alkyl groups whose number of carbon atoms can vary from 1 to a given upper limit, thus also comprise unsaturated alkyl groups whose number of carbon atoms can vary from 2 to the given upper limit. Examples of such residues are the vinyl residue, the 1-propenyl residue, the 2-propenyl residue (allyl residue), the 2-butenyl residue, the 2-methyl-2-propenyl residue, the 3-methyl-2-butenyl residue, the ethinyl residue, the 2-propinyl residue (propargyl residue), the 2-butinyl residue or the 3-butinyl residue. Further, the term alkyl here also expressly includes alkyl residues in which by an internal ring closure within the alkyl group a cyclic system is formed, i.e. the term alkyl also includes saturated and partially unsaturated cycloalkyl residues and cycloalkyl-alkyl- residues (alkyl substituted by cycloalkyl). Of course, a monocyclic cycloalkyl group contains at least three carbon atoms.

Specific alkyl groups whose number of carbon atoms can vary from 1 to a given upper limit, thus also comprise monocyclic cycloalkyl groups whose number of carbon atoms can vary from 3 to the given upper limit, and appropriate cycloalkyl-alkyl- groups. Examples of such cycloalkyl residues are cyclopropyl, cyclobutyl, cyclopentyl, cyclohexyl, cycloheptyl and cyclooctyl which can all also be substituted by one or more identical or different ($C_1$-$C_4$)-alkyl residues, in particular by methyl. Examples of such substituted cycloalkyl residues are 4-methylcyclohexyl, 4-tert-butylcyclohexyl or 2,3-dimethylcyclopentyl. Furthermore, unless stated otherwise the term alkyl here also expressly includes unsubstituted alkyl residues as well as alkyl residues which are substituted by one or more, for example one, two, three or four, identical or different aryl residues. The term alkyl thus here also expressly includes arylalkyl- residues such as, for example, aryl-($C_1$-$C_4$)-alkyl-, for example benzyl residues, phenylethyl residues or indanyl residues. In substituted alkyl residues, for example arylalkyl-, hydroxyalkyl- such as —($C_1$-$C_3$)-alkyl-OH or alkoxyalkyl- such as —($C_1$-$C_3$)-alkyl-O—($C_1$-$C_4$)-alkyl, the substituents can be present in any desired position.

A saturated or partially unsaturated 3-membered to 7-membered carbocycle representing the ring $A^2$ can be derived from the monocyclic parent systems cyclopropane, cyclobutane, cyclopentane, cyclohexane or cycloheptane. If the carbocycle is unsaturated it can contain, for example, one double bond or, in the case of a 5-membered ring, 6-membered ring or 7-membered ring, also two double bonds which can be isolated or conjugated. Double bonds can be present in any positions with respect to the groups C(=X)—NH— and NH—$SO_2$—$R^2$, i.e., for example a double bond can also be present between the two ring carbon atoms which carry these two groups.

Unless stated otherwise, phenyl residues, naphthyl residues and heterocyclic residues, for example heteroaryl residues, can be unsubstituted or can carry one or more, for example one, two, three or four, identical or different substituents which can be in any desired positions. Unless stated otherwise, in these residues for example those substituents can be present which are indicated as substituents of an aryl group. A preferred series of substituents that can be present in the residue aryl is formed by the substituents halogen, ($C_1$-$C_5$)-alkyl, phenyl, tolyl, $CF_3$, $NO_2$, OH, —O—($C_1$-$C_5$)- alkyl, —O—($C_2$-$C_4$)-alkyl-O—($C_1$-$C_3$)-alkyl, ($C_1$-$C_2$)-alkylenedioxy, $NH_2$, —NH—($C_1$-$C_3$)-alkyl, —N(($C_1$-$C_3$)-alkyl)$_2$, —NH—CHO, —NH—CO—($C_1$-$C_5$)-alkyl, —CN, —CO—$NH_2$, —CO—NH—($C_1$-$C_3$)-alkyl, —CO—N(($C_1$-$C_3$)-alkyl)$_2$, —CO—OH, —CO—O—($C_1$-$C_5$)-alkyl, heterocyclyl, CHO, —CO—($C_1$-$C_5$)-alkyl, —S(O)$_n$—($C_1$-$C_4$)-alkyl, —S(O)$_n$-phenyl and —S(O)$_n$-tolyl. If in compounds of the formula I nitro groups are present as substituents, in total only up to two nitro groups can be present in the molecules. If phenyl residues, phenoxy residues, benzyl residues or benzyloxy residues are present as substituents in, for example, aryl residues like phenyl residues and/or in heterocyclic residues then in these substituents the benzene ring can also be unsubstituted or substituted by one or more, for example one, two, three or four, identical or different residues, for example by residues from the series ($C_1$-$C_4$)-alkyl, halogen, hydroxy, ($C_1$-$C_4$)-alkoxy, trifluoromethyl, cyano, hydroxycarbonyl, (($C_1$-$C_4$)-alkoxy)carbonyl, aminocarbonyl, nitro, amino, ($C_1$-$C_4$)-alkylamino, di-(($C_1$-$C_4$)-alkyl)amino and (($C_1$-$C_4$)-alkyl)carbonylamino.

In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. Tolyl (i.e., methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position.

The above explanations as well as the following explanations relating to monovalent residues correspondingly apply to the divalent residues phenylene, naphthylene and heteroarylene. The free bonds via which the divalent residues are attached to the adjacent groups can be present on any ring carbon atoms. In the case of a phenylene residue they can be in 1,2-position (ortho-phenylene), 1,3-position (meta-phenylene) or 1,4-position (para-phenylene). In the case of a naphthylene residue the free bonds can be in 1,2-position (=1,2-naphthylene or 1,2-naphthalinediyl) or in 1,3-position, 1,4-position, 1,5-position, 1,6-position, 1,7-position, 1,8-position, 2,3-position, 2,6-position or 2,7-position. In the case of 5-membered ring aromatics containing one heteroatom such as, for example, thiophene or furan, the two free bonds can be in 2,3-position, 2,4-position, 2,5-position or 3,4-position. A divalent residue derived from pyridine can be a 2,3-, 2,4-, 2,5-, 2,6-, 3,4- or 3,5-pyridinediyl residue. In the case of unsymmetrical divalent residues the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Heteroaryl residues, heteroarylene residues, heterocyclyl residues, heterocycles representing the ring $A^2$ and rings which are formed by two groups bonded to a nitrogen atom together with this nitrogen atom are preferably derived from heterocycles which contain one, two, three or four identical or different ring heteroatoms, more preferably from heterocycles which contain one, two or three, in particular one or two, identical or different heteroatoms. Unless stated otherwise, the heterocycles can be monocyclic or polycyclic, for example monocyclic, bicyclic or tricyclic. Preferably they are monocyclic or bicyclic. The rings preferably are 5-membered rings, 6-membered ring or 7-membered ring. Examples of monocyclic and bicyclic heterocyclic systems from which residues occurring in the compounds of the formula I can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form, insofar as the respective forms are known and stable.

Thus, the heterocycles which are suitable also include, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, one, two or three double bonds within the ring system. 5-membered rings and 6-membered rings can in particular also be aromatic.

The residues derived from these heterocycles can be attached via any suitable carbon atom. Nitrogen heterocycles which can carry a hydrogen atom or a substituent on a ring nitrogen atom, for example pyrrole, imidazole, pyrrolidine, morpholine, piperazine etc., can also be attached via a ring nitrogen atom, in particular if the heterocyclic residue in question is bonded to a carbon atom. For example, a thienyl residue can be present as 2-thienyl residue or 3-thienyl residue, a furyl residue as 2-furyl residue or 3-furyl residue, a pyridyl residue as 2-pyridyl residue, 3-pyridyl residue or 4-pyridyl residue, a piperidinyl residue as 1-piperidinyl residue (i.e., piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (i.e., thiomorpholino residue). A residue derived from 1,3-thiazole or imidazole which is attached via a carbon atom can be attached via the 2-position, the 4-position or the 5-position.

Unless stated otherwise the heterocyclic groups can be unsubstituted or can carry one or more, for example one, two, three, or four, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position. Unless stated otherwise, for example those substituents can be present as substituents in heterocyclic groups which are indicated in the definition of the group aryl, and in the case of saturated and partially unsaturated heterocycles as further substituents also the oxo group and the thioxo group can be present. Substituents on a heterocycle as well as substituents on a carbocycle can also form a ring, i.e., to a ring system further rings can be condensed (or anellated) so that, for example, also cyclopenta-condensed, cyclohexa-condensed or benzo-condensed rings can be present. Suitable substituents on a substitutable ring nitrogen atom of a heterocycle are in particular, for example, unsubstituted $(C_1-C_5)$-alkyl residues and aryl-substituted alkyl. residues, aryl residues, acyl residues such as —CO—$(C_1-C_5)$-alkyl, or sulfonyl residues such as —$SO_2$—$(C_1-C_5)$-alkyl. Suitable nitrogen heterocycles can also be present as N-oxides or as quaternary salts containing a counterion which is derived from a physiologically acceptable acid. Pyridyl residues, for example, can be present as pyridine-N-oxides.

"Halogen" is fluorine, chlorine, bromine or iodine, and preferably fluorine or chlorine.

Without limiting the present invention, in the formulae Ia, Ib, Ic, Id, Ie, If, Ig and Ih examples of groups of compounds of the invention are shown in which $A^2$ in the formula I has specific denotations. $A^1$, $R^1$, $R^2$, $R^3$, X and n in the formulae Ia, Ib, Ic, Id, Ie, If, Ig and Ih are defined as above for the formula I, and the number k in the formula Ib is 1, 2, 3, 4 or 5, in particular 3 or 4.

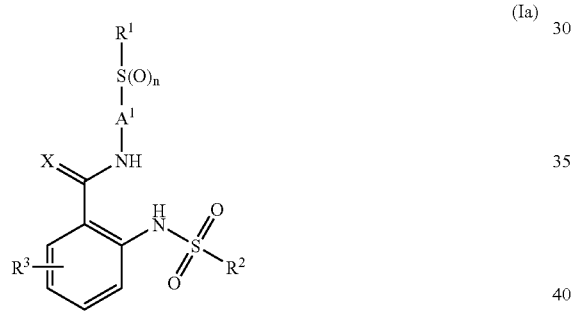
(Ia)

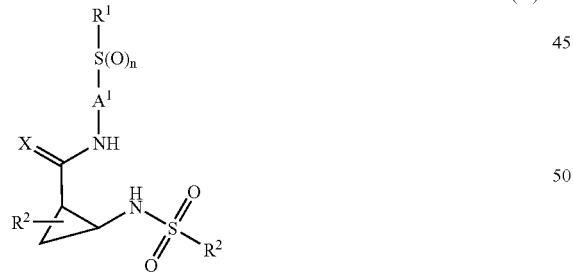
(Ib)

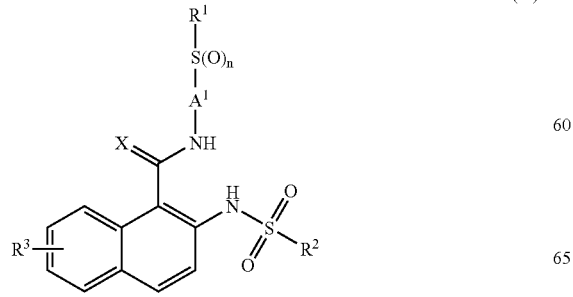
(Ic)

-continued

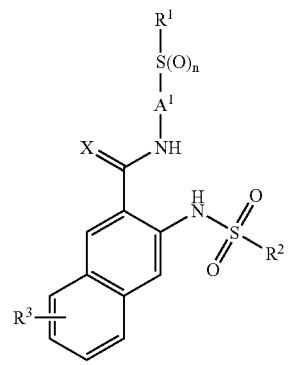
(Id)

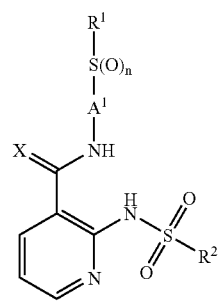
(Ie)

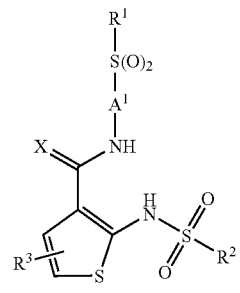
(If)

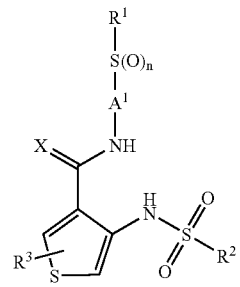
(Ig)

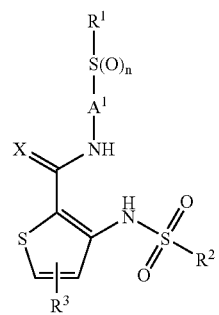
(Ih)

On the benzene ring depicted in formula Ia which carries the groups C(=X)—NH— and —$NHSO_2R^2$, four positions are present which can carry a residue $R^3$. The compounds of formula Ia can thus carry four residues $R^3$ which, independently of one another, can all be hydrogen or can have a meaning different from hydrogen, i.e., in the compounds of formula Ia the benzene ring depicted in formula Ia can be unsubstituted or can carry one, two, three or four identical or different substituents from the series halogen, $CF_3$, OH, —O—$(C_1$-$C_7)$-alkyl, —O—$(C_2$-$C_4)$-alkyl-O—$(C_1$-$C_7)$-alkyl, —O-aryl, $(C_1$-$C_2)$-alkylenedioxy, $NO_2$, —CN, $NR^7R^8$, —CO—$NR^7R^8$, —CO—OH, —CO—O—$(C_1$-$C_5)$-alkyl, heterocyclyl, —S(O)$_n$—$(C_1$-$C_5)$-alkyl and $(C_1$-$C_5)$-alkyl which can be substituted by one or more identical or different residues $R^4$. These explanations accordingly also apply to the compounds of formulae Ib to Ih.

The compounds of the formula I wherein X is a nitrogen atom which via a single bond is attached to a ring carbon atom in the group $A^1$ which ring carbon atom is directly adjacent to the carbon atom in $A^1$ carrying the group —NH—C(=X)— so that the group —NH—C(=X)— together with the carbon atoms in $A^1$ carrying it forms an anellated imidazole ring, are represented by the formula Ii.

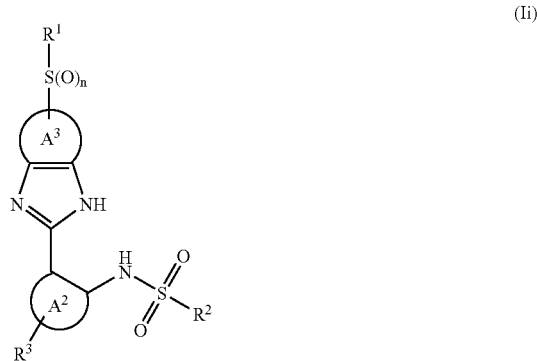

(Ii)

$A^2$, $R^1$, $R^2$, $R^3$ and n in the formula Ii are defined as above for the formula I. The ring $A^3$ which has resulted from the group $A^1$ by the formation of a bond to the nitrogen atom representing X and which ring comprises the two carbon atoms depicted in formula Ii carrying the nitrogen atoms of the anellated imidazole ring, is a benzene ring, a naphthalene ring or a heteroaromatic ring, where to these rings the above explanations relating to $A^1$ correspondingly apply.

The present invention includes all stereoisomeric forms of the compounds of the formula I. Centers of asymmetry that are present in the compounds of formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis. The present invention also includes all tautomeric forms of the compounds of formula I.

If the compounds of the formula I contain one or more acidic or basic groups the invention also includes the corresponding physiologically or toxicologically acceptable salts, in particular the pharmaceutically utilizable salts. Thus, the compounds of the formula I which contain acidic groups can be present on these groups and can be used according to the invention, for example, as alkali metal salts, alkaline earth metal salts or as ammonium salts. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their acid addition salts with inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the formula I simultaneously contain acidic and basic groups in the molecule the invention also includes, in addition to the salt forms mentioned, inner salts or betaines (zwitterions). Salts can be obtained from the compounds of the formula I by customary methods which are known to the person skilled in the art, for example by combination with an organic or inorganic acid or base in a solvent or dispersant, or by anion exchange or cation exchange from other salts. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols, and also derivatives of the compounds of the formula I such as, for example esters, amides, prodrugs and active metabolites.

$A^1$ preferably is a phenylene residue or a 5-membered or 6-membered heteroarylene residue, more preferably phenylene, where all these residues can be unsubstituted or can be substituted as indicated. If the group $A^1$ is substituted, i.e. if it carries one or more further substituents in addition to the group $R^1$—S(O)$_n$, it is preferably substituted by one or two identical or different of the substituents indicated above. Preferably a phenylene residue representing $A^1$ is unsubstituted, i.e. besides the groups $R^1$—S(O)$_n$ and C(=X)—NH it carries four hydrogen atoms. The group $R^1$—S(O)$_n$ is preferably attached to a carbon atom in $A^1$ which is not directly adjacent to the carbon atom which carries the group C(=X)—NH. If $A^1$ is phenylene the group $R^1$—S(O)$_n$ is particularly preferably located in the meta position or in the para position, more particularly preferably in the para position, with respect to the carbon atom which carries the group C(=X)—NH.

The ring $A^2$ which comprises the two carbon atoms which carry the groups $R^2$—SO$_2$—NH and C(=X)—NH— preferably is an aromatic ring, more preferably a benzene ring or a thiophene ring, particularly preferably a benzene ring, where all these rings can be unsubstituted or substituted by one ore more residues $R^3$ which are different from hydrogen.

$R^1$ preferably is $(C_1-C_7)$-alkyl, $NR^5R^6$ or aryl, more preferably $NR^5R^6$, phenyl or 5-membered or 6-membered heteroaryl, particularly preferably $NR^5R^6$, where all these residues can be unsubstituted or substituted as indicated and where, as stated above, $R^1$ can be $NR^5R^6$ if the number n in the group $R^1$—$S(O)_n$— is 2.

$R^2$ preferably is aryl, more preferably phenyl or 5-membered or 6-membered heteroaryl, particularly preferably phenyl or a residue of a monocyclic 5-membered or 6-membered aromatic heterocycle which contains one or two identical or different heteroatoms from the series N, O and S such as, for example, phenyl, thienyl, pyrazolyl, imidazolyl, isoxazolyl, thiazolyl, pyridyl etc., in particular phenyl or 2-thienyl, where all these residues can be unsubstituted or substituted as indicated. Preferably an aryl residue representing $R^2$ is substituted. If an aryl residue representing $R^2$ is substituted it is preferably substituted by one, two or three, in particular by one or two, identical or different substituents. Substituents in an aryl residue representing $R^2$ preferably are substituents from the series halogen, $CF_3$, —O—$CF_3$, $NO_2$, —CN, $(C_1-C_4)$-alkyl and —O—$(C_1-C_4)$, more preferably substituents from the series F, Cl, Br, $CF_3$, —O—$CF_3$, $NO_2$, —CN, $CH_3$ and —$OCH_3$. Especially preferably a substituted aryl residue representing $R^2$ is substituted by Cl, for example by one or two, in particular one, chlorine atoms.

The rings representing $A^2$ can be unsubstituted or substituted as indicated. When they are unsubstituted they only carry residues $R^3$ which are hydrogen. When they are substituted they carry one or more residues $R^3$ which are different from hydrogen. Those substituent positions which do not carry a residue $R^3$ which is different from hydrogen, carry hydrogen atoms. If the ring $A^2$ carries one or more residues $R^3$ which are different from hydrogen it preferably carries one or two such residues $R^3$, in particular one such residue $R^3$. Residues $R^3$ which are different from hydrogen are preferably located in positions of the ring $A^2$ which are not directly adjacent to the groups $C(=X)$—NH and $R^2$—$SO_2$—NH. If $A^2$ is a saturated or partially unsaturated carbocycle, residues $R^3$ which are different from hydrogen preferably are $(C_1-C_4)$-alkyl, in particular methyl. If $A^2$ is an aromatic ring, in particular if $A^2$ is a benzene ring, residues $R^3$ which are different from hydrogen preferably are $(C_1-C_3)$-alkyl, halogen, $(C_1-C_3)$-alkoxy or $CF_3$, more preferably methyl, chlorine or methoxy. If a $A^2$ is an aromatic ring, in particular a benzene ring, it is very particularly preferred if the ring carries one chlorine atom or two methoxy groups as substituents, i.e., if one residue $R^3$ is present which is chlorine or if two residues $R^3$ are present which are methoxy, and the other positions on the benzene ring carry hydrogen atoms. If $A^2$ is a benzene ring residues $R^3$ which are different from hydrogen are preferably located in positions 4 and/or 5 (with respect to the group $C(=X)$—NH in the 1-position and the group $R^2$—$SO_2$—NH in the 2-position).

If a group is substituted by one or more residues $R^4$ it is preferably substituted by one, two or three, in particular one or two, identical or different residues $R^4$. $R^4$ preferably is hydroxy, $(C_1-C_4)$-alkyloxy, di-$((C_1-C_4)$-alkyl)amino or heteroaryl. $R^5$ and $R^6$ preferably are independently of one another hydrogen, $(C_1-C_9)$-alkyl, $(C_1-C_4)$-alkyl-O—$(C_1-C_3)$-alkyl- or 5-membered or 6-membered aryl or together with the nitrogen atom carrying $R^5$ and $R^6$ form a 5-membered to 7-membered heterocycle which in addition to the nitrogen atom carrying the groups $R^5$ and $R^6$ can contain one further ring heteroatom from the series N, O and S and which can be substituted by one or more, for example one, two, three or four, identical or different residues from the series $(C_1-C_3)$-alkyl, hydroxy-$(C_1-C_3)$-alkyl-, 5-membered or 6-membered aryl, carbamoyl, hydroxy and oxo. It is particularly preferred if $R^5$ and $R^6$ together with the nitrogen atom carrying these residues form a 5-membered, 6-membered or 7-membered heterocycle which in addition to the nitrogen atom carrying the groups $R^5$ and $R^6$ can contain one further ring heteroatom from the series N, O and S and which can be substituted by one or more, for example one, two, three or four, identical or different residues from the series $(C_1-C_3)$-alkyl, hydroxy-$(C_1-C_3)$-alkyl-, 5-membered or 6-membered aryl, carbamoyl, hydroxy and oxo, in particular $(C_1-C_3)$-alkyl such as, for example, methyl. Preferably a heterocycle which is formed from the groups $R^1$ and $R^6$ together with the nitrogen atom carrying these residues is saturated.

An especially preferable heterocycle which is formed by $R^1$ and $R^6$ together with the nitrogen atom carrying these residues, is derived from morpholine, thiomorpholine, 1,1-dioxo-thiomorpholine, 1-oxo-thiomorpholine, from dialkylmorpholines such as dimethylmorpholines, from 2,6-dimethylmorpholine, cis-2,6-dimethylmorpholine, 3,5-dimethylmorpholine, cis-3,5-dimethylmorpholine, 1-(pyrimidin-2-yl)-piperazine, piperidine-4-carboxamide, 1-(2-hydroxyethyl)-piperazine, 1-methylpiperazine, 1-ethylpiperazine, from 1-arylpiperazines, from ethyl piperazine-1-carboxylate, piperidine, 2-methylpiperidine, 2,6-dimethylpiperidine, cis-2,6-dimethylpiperidine, 3,5-dimethylpiperidine, cis-3,5-dimethylpiperidine, 4-hydroxypiperidime, from 4-oxopiperidine or a ketal thereof like 1,4-dioxa-8-aza-spiro[4.5]decan, from tetrahydropyridine, tetrahydropyrimidine, 1-methylhomopiperazine, thiazolidine, pyrroline, pyrrolidine, 3-hydroxypyrrolidine, 1,2,3,4-tetrahydroisoquinoline or 2,3-dihydro-1H-isoindole, where these rings are attached via the ring nitrogen atom or, in the case of piperazine derivatives, via the unsubstituted ring nitrogen atom. A more especially preferable heterocycle which is formed by $R^1$ and $R^6$ together with the nitrogen atom carrying these residues, is derived from morpholine, thiomorpholine, 1,1-dioxo-thiomorpholine, 1-oxo-thiomorpholine, 2,6-dimethylmorpholine, cis-2,6-dimethylmorpholine, 3,5-dimethylmorpholine, cis-3,5-dimethylmorpholine, 1-(pyrimidin-2-yl)piperazine, piperidine-4-carboxamide, 1,2,3,4-tetrahydroisoquinoline or 2,3-dihydro-1H-isoindole, moreover preferably from morpholine, 2,6-dimethylmorpholine or cis-2,6-dimethylmorpholine, in particular from morpholine or cis-2,6-dimethylmorpholine, where these rings are attached via the ring nitrogen atom or, in the case of the piperazine derivative, via the unsubstituted ring nitrogen atom.

$R^7$ preferably is hydrogen, $(C_1-C_3)$-alkyl, $((C_1-C_4)$-alkyl$)_2$N-$(C_1-C_3)$-alkyl- or $(C_1-C_4)$-alkyl-O—$(C_1-C_3)$-alkyl-.

$R^8$ preferably is hydrogen, $(C_1-C_3)$-alkyl or acetyl.

Aryl preferably is phenyl or heteroaryl, in particular phenyl or 5-membered or 6-membered heteroaryl. Unless stated otherwise, preferred substituents on aryl residues are halogen, $CF_3$, $(C_1-C_3)$-alkyl, cyano, nitro and $(C_1-C_3)$-alkyloxy, more preferred substituents are $CF_3$, chlorine, methyl and methoxy.

Heteroaryl and heteroarylene preferably are a residue of a monocyclic 5-membered or 6-membered aromatic heterocycle, in particular a residue derived from the heteroaromatics thiophene, pyrazole, thiazole, oxazole, isoxazole, pyridine, pyrimidine, pyridazine and tetrazole.

Heterocyclyl preferably is a residue derived from a saturated heterocycle, more preferably a residue of a monocyclic 5-membered or 6-membered saturated heterocycle, in particular a residue which is derived from pyrrolidine, piperidine, from N-alkylpiperazines, from morpholine, from dialkylmorpholines, from thiomorpholine or tetrahydrofuran. In addition, the above explanations on preferred heterocycles which are formed by the residues $R^5$ and $R^6$ together with the nitrogen atom carrying these residues correspondingly apply to heterocyclyl residues which are attached via a ring nitrogen atom.

If a group $S(O)_n$ is bonded to a nitrogen atom the number n therein preferably is 1 or 2, more preferably 2. The number n in the group $R^1$—$S(O)_n$ preferably is 0 or 2, particularly preferably 2.

X preferably is O or a nitrogen atom which via a single bond is attached to a ring carbon atom in the group $A^1$ which ring carbon atom is directly adjacent to the carbon atom in $A^1$ carrying the group —NH—C(=X)— so that the group —NH—C(=X)— together with the carbon atoms in $A^1$ carrying it forms an anellated imidazole ring. Particularly preferably X is O.

Preferred compounds of the formula I are those compounds in which one or more of the residues contained therein have preferred meanings, all combinations of preferred substituent definitions being a subject of the present invention. Also with respect to all preferred compounds of the formula I the present invention includes all stereoisomeric forms and mixtures thereof in all ratios, and their physiologically acceptable salts. Groups of preferred compounds are also formed, for example, by the compounds of the formulae Ia, Ib, Ic, Id, Ie, If, Ig and Ih in which one or more residues have preferred meanings, in all their stereoisomeric forms and mixtures thereof in all ratios, and their physiologically acceptable salts.

A group of particularly preferred compounds is formed, for example, by compounds of the formula I in which $A^1$ is phenylene or heteroarylene where these residues can be unsubstituted or substituted by one or more identical or different substituents from the series halogen, $(C_1$-$C_4)$-alkyl, $CF_3$, —O—$(C_1$-$C_4)$-alkyl and —CN;

the ring $A^2$ which comprises the two carbon atoms which carry the groups $R^2$—$SO_2$—NH and C(=X)—NH— is an aromatic ring;

$R^1$ is $(C_1$-$C_7)$-alkyl which can be substituted by one or more identical or different residues $R^4{}_1$, or is aryl, or if the number n in the group $R^1$—$S(O)_n$—is 2 also is $NR^5R^6$;

$R^2$ is aryl;

$R^3$ denotes one or more identical or different residues from the series hydrogen, halogen, $CF_3$, OH, —O—$(C_1$-$C_4)$-alkyl, —O—$(C_2$-$C_4)$-alkyl-O—$(C_1$-$C_4)$-alkyl, —O-aryl, $NO_2$, —CN, $NR^7R^8$, —CO—$NR^7R^8$, —CO—OH, —CO—O—$(C_1$-$C_4)$-alkyl, heterocyclyl, —$S(O)_n$—$(C_1$-$C_4)$-alkyl and $(C_1$-$C_4)$-alkyl which can be substituted by one or more identical or different residues $R^4$;

$R^4$ is fluorine, OH, —O—$(C_1$-$C_{10})$-alkyl, O—$(C_2$-$C_4)$-alkyl-O—$(C_1$-$C_7)$-alkyl, —O-aryl, —CN, $NR^7R^8$, —CO—$NH_2$, —CO—NH—$(C_1$-$C_3)$-alkyl, —CON—$((C_1$-$C_3)$-alkyl$)_2$, —CO—OH, —CO—O—$(C_1$-$C_4)$-alkyl, heterocyclyl or oxo;

$R^5$ and $R^6$ independently of one another are hydrogen, $(C_1$-$C_9)$-alkyl, $(C_1$-$C_4)$-alkyl-O—$(C_1$-$C_3)$-alkyl- or aryl or together with the nitrogen atom carrying $R^5$ and $R^6$ form a 5-membered to 7-membered heterocycle which in addition to the nitrogen atom carrying the groups $R^5$ and $R^6$ can contain one further ring heteroatom from the series N, O and S and which can be substituted by one or more identical or different residues from the series $(C_1$-$C_3)$-alkyl, hydroxy-$(C_1$-$C_3)$-alkyl-, aryl, carbamoyl, hydroxy and oxo;

$R^7$ is hydrogen, $(C_1$-$C_3)$-alkyl, $((C_1$-$C_4)$-alkyl$)_2N$—$(C_1$-$C_3)$-alkyl- or $(C_1$-$C_4)$-alkyl-O—$(C_1$-$C_3)$-alkyl-;

$R^8$ is hydrogen, $(C_1$-$C_3)$-alkyl or acetyl;

"aryl" is phenyl or heteroaryl which can all be substituted by one or more identical or different substituents from the series halogen, $(C_1$-$C_4)$-alkyl, phenyl, $CF_3$, $NO_2$, —O—$(C_1$-$C_4)$-alkyl, $(C_1$-$C_2)$-alkylenedioxy, $NH_2$, —NH—CO—$(C_1$-$C_4)$-alkyl, —CN, —CO—$NH_2$, —CO—OH and —CO—O—$(C_1$-$C_4)$-alkyl;

heteroaryl and heteroarylene are a residue of a monocyclic 5-membered or 6-membered aromatic heterocycle which contains one or more identical or different ring heteroatoms from the series N, O and S;

heterocyclyl is a residue of a monocyclic 5-membered or 6-membered saturated heterocycle which contains one or more identical or different ring heteroatoms from the series N, O and S and which can be substituted by one or more identical or different substituents from the series fluorine, $(C_1$-$C_4)$-alkyl, OH, —O—$(C_1$-$C_4)$-alkyl, $NH_2$, —CN, —CO—$NH_2$, —CO—OH and —CO—O—$(C_1$-$C_4)$-alkyl;

n is 0, 1 or 2;

X is oxygen;

in all their stereoisomeric forms and mixtures thereof in all ratios, and their physiologically acceptable salts.

A group of more particularly preferred compounds is formed, for example, by compounds of the formula I in which:

$A^1$ is phenylene which is unsubstituted or substituted by one or more identical or different substituents from the series halogen, $(C_1$-$C_4)$-alkyl, $CF_3$, —O—$(C_1$-$C_4)$-alkyl and —CN;

the ring $A^2$ which comprises the two carbon atoms which carry the groups $R^2$—$SO_2$—NH and C(=X)—NH— is a benzene ring;

$R^1$ is $NR^5R^6$;

$R^2$ is aryl;

$R^3$ denotes one or more identical or different residues from the series hydrogen, halogen, $CF_3$, —O—$(C_1$-$C_4)$-alkyl, —CN and $(C_1$-$C_4)$-alkyl;

$R^5$ and $R^1$ together with the nitrogen atom carrying $R^5$ and $R^6$ form a 5-membered or 6-membered saturated heterocycle which in addition to the nitrogen atom carrying the groups $R^5$ and $R^6$ can contain one further ring heteroatom from the series N, O and S and which can be substituted by one or more identical or different residues from the series $(C_1$-$C_3)$-alkyl, hydroxy-$(C_1$-$C_3)$-alkyl-, aryl, carbamoyl, hydroxy and oxo;

aryl is phenyl or 5-membered or 6-membered heteroaryl containing one or more identical or different ring heteroatoms from the series N, O and S which residues can all be substituted by one or more identical or different substituents from the series halogen, $(C_1$-$C_4)$-alkyl, $CF_3$, $NO_2$, —O—$(C_1$-$C_4)$-alkyl, —NH—CO—$(C_1$-$C_4)$-alkyl and —CN;

n is 2;

X is oxygen;

in all their stereoisomeric forms and mixtures thereof in all ratios, and their physiologically acceptable salts.

A group of especially preferred compounds is formed, for example, by compounds of the formula I in which:

$A^1$ is an unsubstituted divalent phenylene residue;

the ring $A^2$ which comprises the two carbon atoms which carry the groups $R^2$—$SO_2$—NH and C(=X)—NH— is a benzene ring;

$R^1$ is $NR^5R^6$;

$R^2$ is aryl;

$R^3$ denotes one or more identical or different residues from the series hydrogen, halogen, —O—$(C_1$-$C_4)$-alkyl and $(C_1$-$C_4)$-alkyl;

$R^5$ and $R^6$ together with the nitrogen atom carrying $R^5$ and $R^6$ form a saturated 6-membered heterocycle which in addition to the nitrogen atom carrying the groups $R^5$ and $R^6$ can contain one further ring heteroatom from the series N, O and S and which can be substituted by one or more identical or different residues from the series $(C_1$-$C_3)$-alkyl, aryl, oxo and carbamoyl;

aryl is phenyl or 5-membered or 6-membered heteroaryl containing one or more identical or different ring heteroatoms from the series N, O and S which residues can all be substituted by one or more identical or different substituents from the series halogen, $(C_1$-$C_4)$-alkyl, $CF_3$ and —O—$(C_1$-$C_4)$-alkyl;

n is 2;

X is oxygen;

in all their stereoisomeric forms and mixtures thereof in all ratios, and their physiologically acceptable salts.

A group of even more preferred compounds is formed, for example, by compounds of the formula I in which:

$A^1$ is an unsubstituted divalent 1,4-phenylene residue;

the ring $A^2$ which comprises the two carbon atoms which carry the groups $R^2$—$SO_2$—NH and C(=X)—NH—, together with the residues $R^3$, is a benzene ring which carries one or two substituents from the series chlorine and methoxy;

$R^1$ is $NR^5R^6$;

$R^2$ is phenyl or thienyl which residues are all substituted by one or two chlorine atoms;

$R^5$ and $R^6$ together with the nitrogen atom carrying $R^5$ and $R^6$ form a saturated 6-membered heterocycle which in addition to the nitrogen atom carrying the groups $R^5$ and $R^6$ can contain one further ring heteroatom from the series O and S and which is unsubstituted or substituted by one or two methyl residues;

n is 2;

X is oxygen;

in all their stereoisomeric forms and mixtures thereof in all ratios, and their physiologically acceptable salts.

The presents invention also relates to processes for the preparation of the compounds of the formula I which are described in the following and by which the compounds of the invention are obtainable. According to Scheme 1 compounds of the invention can be obtained, for example, by first reacting an aminocarboxylic acid of the formula II with a sulfonyl chloride of the formula $R^2$—$SO_2$—Cl or a sulfonic acid anhydride in the presence of a base in a solvent like water, pyridine or an ether. Suitable bases are inorganic bases like sodium carbonate or organic bases like, for example, pyridine or triethylamine. The sulfonylaminocarboxylic acid of the formula III that is obtained can then be activated, for example by reaction with a chlorinating agent like phosphorus pentachloride, phosphorus oxychloride or thionyl chloride in an inert solvent, to give an acid chloride of the formula IV which is then reacted with an arylamine.

The activation of the carboxylic acid group in the compounds of the formula III can, however, also be carried out in a different manner, for example by one of the numerous methods for the formation of amide bonds in peptide chemistry which are well-known to the skilled person, for example by conversion into a mixed anhydride or an activated ester or by using a carbodiimide like dicyclohexylcarbodimide.

The reaction of the activated sulfonylaminocarboxylic acid with an arylamine is favorably carried out in an inert solvent such as, for example, pyridine, tetrahydrofuran or toluene in the absence or in the presence of an inert auxiliary base like, for example, a tertiary amine or pyridine. If the arylamine that is employed in the reaction with the activated carboxylic acid already contains the desired substituent $R^1$—S(O)$_n$ then the reaction directly provides the final compound of the formula I. Compounds of the formula I in which the number n in the group $R^1$—S(O)$_n$ is 1 or 2 can also be obtained by reacting an activated carboxylic acid with a mercapto substituted arylamine of the formula $R^1$—S—$A^1$—$NH_2$ and then oxidizing the mercapto group in the compound of the formula V under standard conditions, for example with a peroxide like hydrogen peroxide or a peracid like 3-chloroperbenzoic acid or monoperoxyphthalic acid in a solvent like, for example, methylene chloride or acetone. The activated carboxylic acids can also first be reacted with arylamines of the formula $A^1$—$NH_2$. The resulting reaction product of the formula VI can then be chlorosulfonated under standard conditions and the chlorosulfonyl group can then be converted under standard conditions into the group $R^1$—$SO_2$, for example by reaction with suitable amines in substance or in a solvent like N-methylpyrrolidone, dimethylformamide, toluene or an ether, optionally in the presence of an auxiliary base. In a similar manner the activated carboxylic acids can be reacted with fluorosulfonylarylamines of the formula F—$SO_2$—A—$NH_2$ and the fluorosulfonyl intermediates of the formula VII that are obtained can be converted under standard conditions into the compounds of the formula I according to the invention.

(Scheme 1)

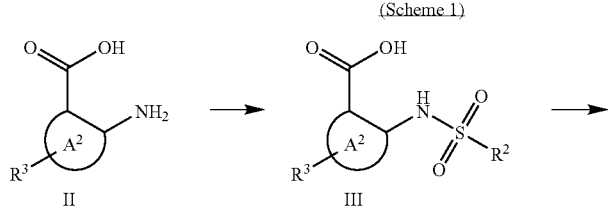

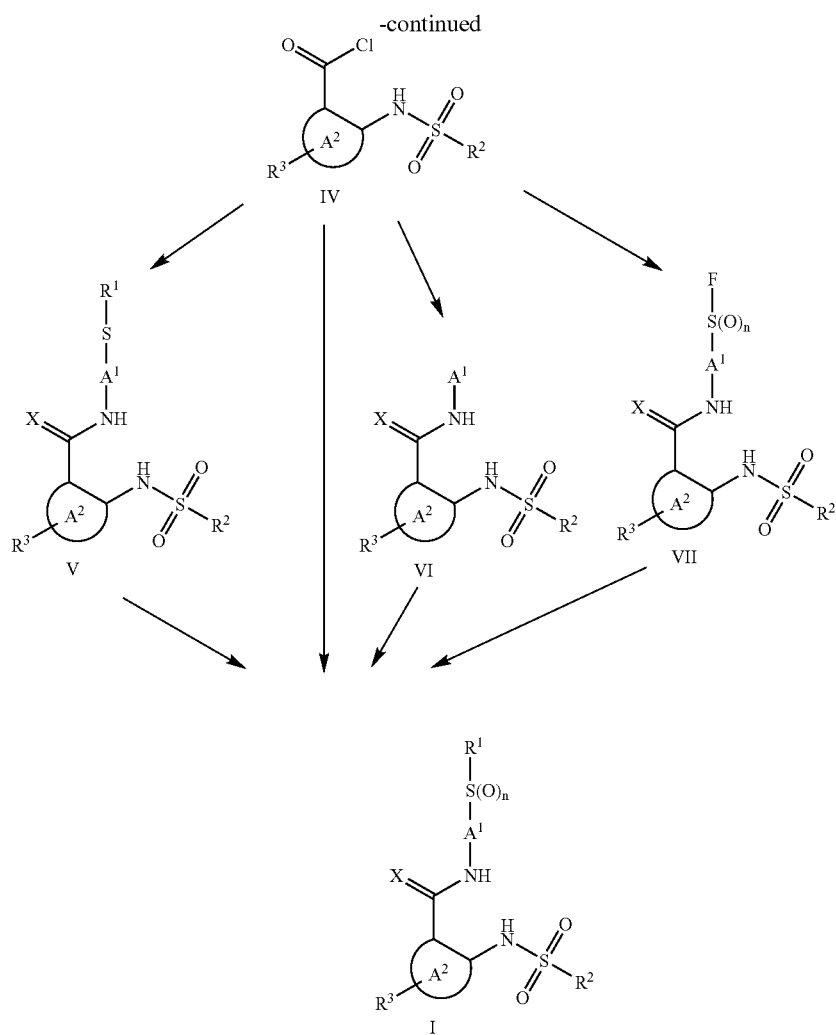

The compounds of the formula I according to the invention can furthermore be obtained by reacting the activated sulfonylaminocarboxylic acids, for example the acid chlorides of the formula IV shown in Scheme 1, with a mercaptoarylamine of the formula $H_2N—A^1—SH$ which is unsubstituted on the sulfur atom. In a nucleophilic substitution reaction the product of the formula VIII that is obtained can subsequently be alkylated or arylated on the sulfur atom with an alkyl halogenide or an aryl halogenide or another reactive compound under standard conditions and, if desired, be oxidized on the sulfur to give the sulfoxide or the sulfone as explained above with respect to the compounds of the formula V (see Scheme 2).

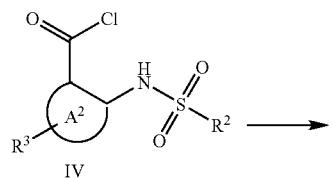

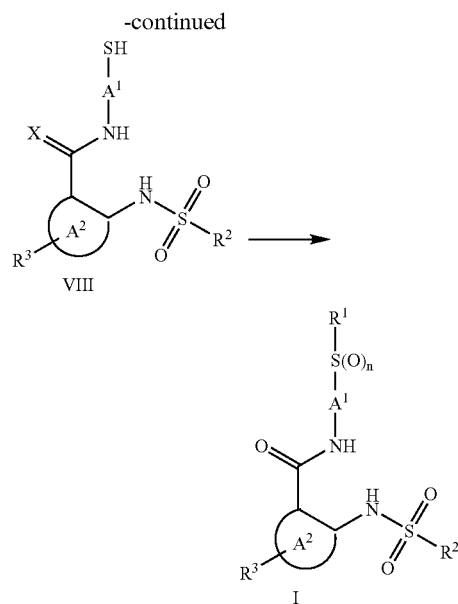

Compounds of the formula I can also be obtained, for example, by first activating a suitably substituted nitrocarboxylic acid of the formula IX, for example by converting it into the respective acid chloride of the formula X or by another procedure, and then reacting it with a substituted arylamine of the formula $R^1$—$S(O)_n$—$A^1$—$NH_2$ analogously to the procedures described above (see Scheme 3). Here, too, as arylamines fluorosulfonylarylamines of the formula F—$SO_2$—$A^1$—$NH_2$ can be employed, and in the N-(fluorosulfonylaryl)-carboxamides of the formula XI that are obtained the fluorosulfonyl group can be converted under standard conditions into a group $R^1$—$SO_2$ according to the invention, for example with an amine of the formula $HNR^5R^6$.

nucleophile, for example an amine. The reduction of the nitro group to give an amino group can, for example, be carried out by catalytic hydrogenation in the presence of a noble metal catalyst or, preferably, in the presence of Raney nickel in a solvent like ethanol, glacial acetic acid or an ethanolic solution of hydrogen chloride, or it can be carried out by reduction with a base metal like zinc, tin or iron in the presence of an acid. The reduction can also be carried out, for example, with tin(II) chloride or by reaction with sodium dithionite, favorably in a mixture of methanol, tetrahydrofuran and water as solvent. The sulfonylation of the amino group in the reduction product of the formula XIII with an activated sulfonic acid derivative can be carried out analo-

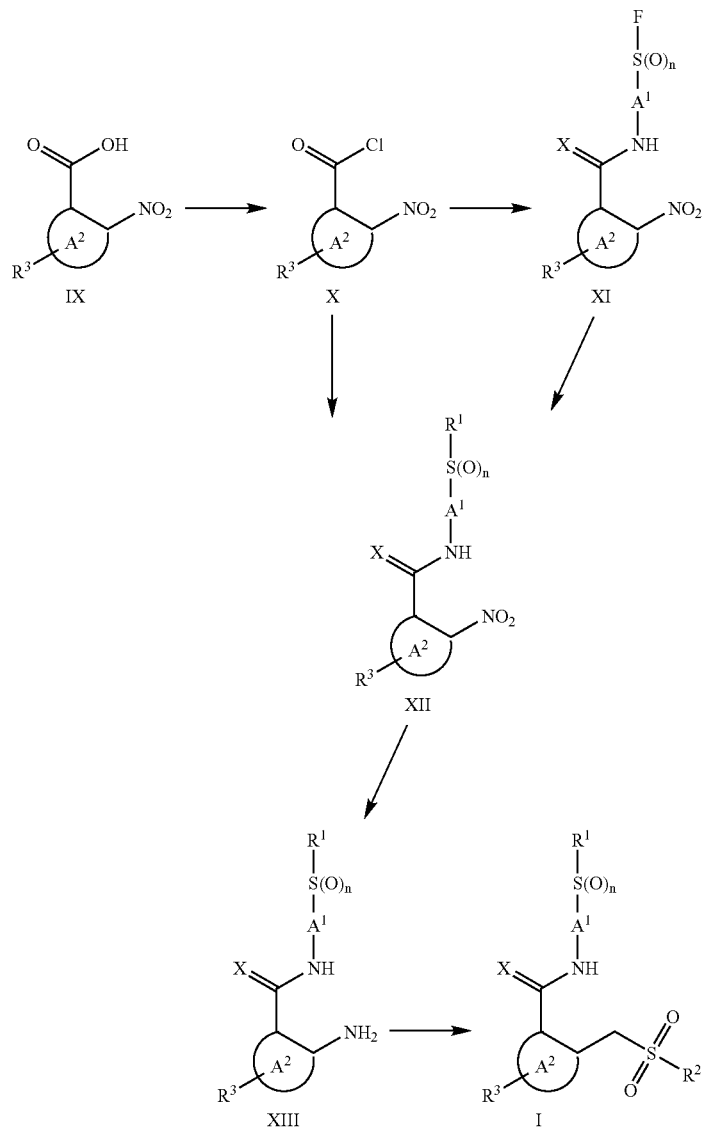

(Scheme 3)

Before the nitro group is reduced to an amino group, in the nitro intermediates of the formula XII, use can be made of the activating effect of the nitro group on the ring $A^2$ and a suitable residue $R^3$, for example a halogen atom, can be replaced with a different residue $R^3$ by reaction with a gously to the reactions described above, for example with a sulfonic acid chloride in pyridine, and finally gives the compound of the formula I.

The compounds of the formula I in which X is a nitrogen atom which via a single bond is attached to a ring carbon atom in the group $A^1$ which ring carbon atom is directly adjacent to the carbon atom in $A^1$ carrying the group —NH—C(=X)—, i.e. the benzimidazole derivatives of the formula Ii, can for example be obtained by reacting an activated sulfonylaminocarboxylic acid derivative obtained as described above according to Scheme 1, for example a carboxylic acid chloride of the formula IV, (or also, in analogy to Scheme 3, a nitrocarboxylic acid derivative) with a 1,2-diaminoarene in the presence of a dehydrating agent such as, for example, thionyl chloride or phosphorus pentachloride (see Scheme 4). The reaction is usually carried out in an inert solvent, for example in a hydrocarbon like toluene or xylene. The 1,2-diaminoarene can already contain the final group $R^1$—S(O)$_n$ or a precursor group thereof, for example the group $R^1$—S. Subsequent steps, for example reactions on the sulfur atom, can then be carried out as explained above. Just so, unsubstituted 1,2-diaminoarenes can be employed and the resulting products of the formula XIV can be chlorosulfonated, for example with chlorosulfuric acid, and the sulfonyl chlorides that are obtained can be converted into the final compounds containing the group $R^1$—SO$_2$, for example by reaction with a suitable amine.

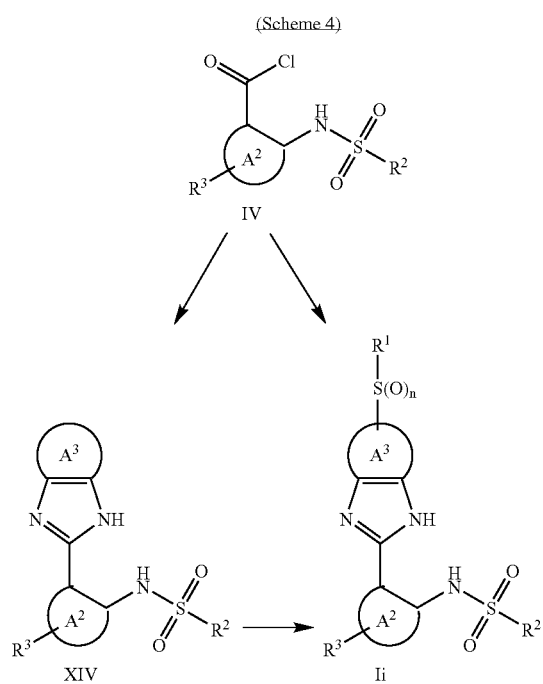

All reactions for the synthesis of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula I it can be necessary or advantageous to temporarily block functional groups by introducing protective groups and to deprotect them in a later stage of the synthesis, or introduce functional groups in the form of precursor groups which in a later reaction step are converted into the desired functional groups. Such synthetic strategies and protective groups and precursor groups which are suitable in an individual case are known to the skilled person. If desired the compounds of the formula I can be purified by customary purification procedures, for example by recrystallization or chromatography. The starting compounds for the preparation of the compounds of the formula I are commercially available or can be prepared according to or analogously to literature procedures.

The compounds of the formula I according to the invention effect an increase of the cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of the formula I can be examined, for example, in the activity assay described below.

Disorders and pathological conditions which are associated with a low cGMP level or in which an increase of the cGMP level is desired and for whose therapy and prophylaxis it is possible to use compounds of the formula I are, for example, cardiovascular diseases, such as endothelial dysfunction, diastolic dysfunction, atherosclerosis, hypertension stable and unstable angina pectoris, thromboses, restenoses, myocardial infarction, strokes, cardiac insufficiency or pulmonary hypertonia, or, for example, erectile dysfunction, asthma bronchiale, chronic kidney insufficiency and diabetes. Compounds of the formula I can additionally be used in the therapy of cirrhosis of the liver and also for improving a restricted memory performance or ability to learn.

The compounds of the formula I and their physiologically acceptable salts can be administered to animals, preferably to mammals, and in particular to humans, as pharmaceuticals by themselves, in mixtures with one another or in the form of pharmaceutical preparations. A subject of the present invention therefore also are the compounds of the formula I and their physiologically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

Furthermore, a subject of the present invention are pharmaceutical preparations (or pharmaceutical compositions) which comprise as active component an effective dose of at least one compound of the formula I and/or a physiologically acceptable salt thereof and a customary pharmaceutically acceptable carrier, i.e. one or more pharmaceutically acceptable carrier substances and/or additives. A subject of the present invention is also those compounds of the formula I which were already known per se and which are excluded by disclaimer from the above-defined compounds of the formula I which are per se a subject of the present invention, and their physiologically acceptable salt as activators of soluble guanylate cyclase.

All statements above and below relating to the pharmacological effects and the uses of the compounds of the formula I thus also apply to the compound of the formula I wherein simultaneously the ring $A^2$ which comprises the carbon atoms which carry the groups C(=X)—NH— and NH—SO$_2$R$^2$ is a benzene ring which is substituted in positions 3 and 5 by chlorine, $R^2$ is methyl, X is oxygen and $R^1$—S(O)$_n$—$A^1$— is a 5-chloro-2-(4-chlorophenylmercapto)-phenyl residue, and its physiologically acceptable salts.

Thus, a subject of the invention are, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt-thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions-, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the formula I and/or its physiologically acceptable salts in the pharmaceutical preparations normally is from 0.2 to 500 mg, preferably from 1 to 200 mg, per dose, but depending on the type of the pharmaceutical preparation it can also be higher. The pharmaceutical preparations usually comprise 0.5 to 90 percent by weight of the compounds of the formula I and/or their physiologically acceptable salts. The preparation of the pharmaceutical preparations can be carried out in a manner known per se. For this purpose, one or more compounds of the formula I and/or their physiologically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I and their physiologically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the formula I to be administered and/or of a physiologically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula I. In general, a daily dose of approximately 0.01 to 100 mg/kg, preferably 0.1 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the formula I activate the soluble guanylate cyclase, mainly by binding in the heme binding pocket of the enzyme. On account of this property, apart from use as pharmaceutically active compounds in human medicine and veterinary medicine, they can also be employed as a scientific tool or as aids for biochemical investigations in which such an effect on guanylate cyclase is intended, and also for diagnostic purposes, for example in the in vitro diagnosis of cell samples or tissue samples. The compounds of the formula I and salts thereof can furthermore be employed, as already mentioned above, as intermediates for the preparation of other pharmaceutically active compounds.

The following examples of compounds of the formula I and of intermediates for their preparation illustrate the invention without limiting it.

EXAMPLES

1.) 2-(4-Chloro-phenylsulfonylamino)-4,5-dimethoxy-benzoic acid 33.71 g (0.32 mol) of sodium carbonate were dissolved in 250 ml of water and warmed to 60° C. 25.00 g (0.13 mol) of 2-amino-4,5-dimethoxy-benzoic acid were introduced into the solution, and to this solution 29.55 g (0.14 mol) of 4-chloro-benzenesulfonyl chloride were added portionwise over 15 min. After cooling the mixture was filtered with suction, the residue was taken up in 1% sodium hydrogencarbonate solution, the solution filtered, and the product precipitated by addition of 1 N hydrochloric acid. 25.90 g (55%) of 2-(4-chloro-phenylsulfonylamino)-4,5-dimethoxy-benzoic acid of melting point (m.p.) 212-214° C. were obtained.

Analogously were obtained:

2.) 5-Chloro-2-(4-chloro-phenylsulfonylamino)-benzoic acid; M.p.: 210° C.

3.) 5-Chloro-2-(3,4-dichloro-phenylsulfonylamino)-benzoic acid

5.) 2-(4-Chloro-phenylsulfonylamino)-cyclopentanecarboxylic acid; M.p.: 147° C.

6.) 2-(4-Chloro-phenylsulfonylamino)-5-methyl-benzoic acid; M.p.: 201° C.

7.) 3-(4-Chloro-phenylsulfonylamino)-thiophene-2-carboxylic acid; M.p.: 180° C.

8.) 3-(4-Chloro-phenylsulfonylamino)-pyrazole-4-carboxylic acid; Oil

9.) 2-(4-Chloro-phenylsulfonylamino)-pyridine-3-carboxylic acid; M.p.: Decomposition (dec.) >360° C.

10.) 2-(4-Chloro-phenylsulfonylamino)-4,5-dimethoxy-benzoyl chloride 25.90 g (0.07 mol) of 2-(4-chloro-phenylsulfonylamino)-4,5-dimethoxy-benzoic acid were mixed with 75 ml of toluene, 17.30 g (0.08 mol) of phosphorus pentachloride were added and the mixture was stirred at 40-45° C. for 2.5 h. Then the mixture was concentrated in vacuo to half of its volume and the product that precipitated was filtered off with suction and washed with a small amount of toluene. 25.30 g (93%) of 2-(4-chloro-phenylsulfonylamino)-4,5-dimethoxy-benzoyl chloride having a melting point of 175-177° C. were obtained.

Analogously were obtained:

11.) 5-Chloro-2-(4-chloro-phenylsulfonylamino)-benzoyl chloride; M.p.: 127° C.

12.) 5-Chloro-2-(3,4-dichloro-phenylsulfonylamino)-benzoyl chloride; M.p.: 117° C.

13.) 2-(4-Chloro-phenylsulfonylamino)-cyclopentanecarboxylic acid chloride; M.p.: 107° C.

14.) 2-(4-Chloro-phenylsulfonylamino)-5-methyl-benzoyl chloride; M.p.: 114° C.

15.) 3-(4-Chloro-phenylsulfonylamino)-thiophene-2-carboxylic acid chloride; M.p.: 122° C.

16.) 3-(4-Chloro-phenylsulfonylamino)-pyrazole-4-carboxylic acid chloride; M.p.: 260° C. (Dec.)

17.) 2-(4-Chloro-phenylsulfonylamino)-pyridine-3-carboxylic acid chloride

18.) 4-((2-(4-Chloro-phenylsulfonylamino)4,5-dimethoxy-benzoyl)-amino)-benzenesulfonyl fluoride 10.00 g (25.6 mmol) of 2-(4-Chloro-phenylsulfonylamino)4,5-dimethoxy-benzoyl chloride were mixed with 300 ml of toluene, 4.49 g (25.6 mmol) of 4-aminobenzenesulfonyl fluoride were added and the mixture was heated under reflux for 4 h. After cooling the precipitated solid was filtered off with suction and washed with toluene. 11.71 g (87%) of the title compound having a melting point of 216-219° C. were obtained.

Analogously were obtained:

19.) 4-((5-Chloro-2-(4-chloro-phenylsulfonylamino)-benzoyl)-amino)-benzenesulfonyl fluoride; M.p.: 242° C.

20.) N-(4-Aminosulfonyl-phenyl)-5-chloro-2-(4-chloro-phenylsulfonylamino)-benzamide; M.p.: 260° C.

21.) 5-Chloro-2-(4-chloro-phenylsulfonylamino)-N-((4-(4-nitro-phenyl)-mercapto)-phenyl)-benzamide; M.p.: 255° C.

22.) 5-Chloro-2-(4-chloro-phenylsulfonylamino)-N-(4-(phenylmercapto)-phenyl)-benzamide; M.p.: 169° C.

23.) 5-Chloro-2-(4-chloro-phenylsulfonylamino)-N-(4-methylmercapto-phenyl)-benzamide; M.p.: 220° C.

24.) 5-Chloro-2-(4-chloro-phenylsulfonylamino)-N-(2-methyl-benzothiazol-5-yl-benzamide; M.p.: 251° C.

25.) 5-Chloro-2-(4-chloro-phenylsulfonylamino)-N-(4-(3-diethylamino-2-hydroxy-propyl-mercapto)-phenyl)-benzamide; M.p.: 102° C.

26.) 4-((5-Chloro-2-(3,4-dichloro-phenylsulfonylamino)-benzoyl)-amino)-benzenesulfonyl fluoride; M.p.: 232° C.

27.) 4-(2-(4-Chloro-phenylsulfonylamino)-cyclopentanecarbonylamino)-benzenesulfonyl fluoride; M.p.: 211° C.

28.) 4-((2-(4-Chloro-phenylsulfonylamino)-5-methyl-benzoyl)-amino)-benzenesulfonyl fluoride; M.p.: 224° C.

29.) 4-((3-(4-Chloro-phenylsulfonylamino)-thiophene-2-carbonyl)-amino)-benzenesulfonyl fluoride; M.p.: 255° C.

30.) 5-Chloro-2-(4-chloro-phenylsulfonylamino)-N-(4-mercapto-phenyl)-benzamide; M.p.: 202° C.

31.) 4-((3-(4-Chloro-phenylsulfonylamino)-pyrazol-4-carbonyl)-amino)-benzenesulfonyl fluoride; M.p.: 251° C.

32.) 3-((5-Chloro-2-(4-chloro-phenylsulfonylamino)-benzoyl)-amino)-benzenesulfonyl fluoride; M.p.: 224° C.

33.) 4-(2-(4-Chloro-phenylsulfonylamino)-pyridine-3-carbonyl)-amino)-benzenesulfonyl fluoride; M.p.: 263-265° C.

34.) 5-Chloro-2-(4-chloro-phenylsulfonylamino)-N-(4-methyl-5-(thiomorpholine-4-sulfonyl)-thiazol-2-yl)-benzamide; M.p.: 265-267° C.

35.) 5-Chloro-2-(4-chloro-phenylsulfonylamino)-N-(2-methylmercapto-phenyl)-benzamide 36.) 5-Chloro-2-(4-chloro-phenylsulfonylamino)-N-(3-methylmercapto-phenyl)-benzamide 37.) 5-Chloro-2-(4-chloro-phenylsulfonylamino)-N-(4-(5-methyl-isoxazol-3-yl-sulfamoyl)-phenyl)-benzamide 38.) 5-Chloro-2-(4-chloro-phenylsulfonylamino)-N-(4-(4-nitro-phenylsulfonyl)-phenyl-benzamide 39.) 5-Chloro-2-(4-chloro-phenylsulfonylamino)-N-(5-ethylsulfonyl-2-hydroxy-phenyl)-benzamide 40.) N-(3-Butylsulfamoyl-phenyl)-5-chloro-2-(4-chlorophenylsulfonylamino)-benzamide 41.) 5-Chloro-2-(4-chloro-phenylsulfonylamino)-N-(2-nitro-5-propylmercapto-phenyl)-benzamide 42.) 5-Chloro-2-(4-chloro-phenylsulfonylamino)-N-(4-thiocyanato-phenyl)-benzamide 43.) N-(4-Acetylsulfamoyl-phenyl)-5-chloro-2-(4-chlorophenylsulfonylamino)-benzamide 44.) 5-Chloro-2-(4-chloro-phenylsulfonylamino)-N-(2-phenylmercapto-phenyl)-benzamide 45.) 5-Chloro-2-(4-chloro-phenylsulfonylamino)-N-(2-chloro-5-(2-cyano-ethylsulfamoyl)-phenyl)-benzamide 46.) N-(5-Butylsulfamoyl-2-methoxy-phenyl)-5-chloro-2-(4-chloro-phenylsulfonylamino)-benzamide 47.) N-(4-Benzoylsulfamoyl-phenyl)-5-chloro-2-(4-chlorophenylsulfonylamino)-benzamide 48.) 5-Chloro-2-(4-chloro-phenylsulfonylamino)-N-(2-chloro-4-methylsulfonyl-phenyl)-benzamide 49.) 5-Chloro-2-(4-chloro-phenylsulfonylamino)-N-(4-(hexadecylsulfonyl)-phenyl)-benzamide 50.) 5-Chloro-2-(4-chloro-phenylsulfonylamino)-N-(4-(butylaminocarbonylaminosulfonyl)-phenyl)-benzamide 51.) 5-Chloro-2-(4-chloro-phenylsulfonylamino)-N-(2-sulfamoyl-phenyl)-benzamide 52.) 5-Chloro-2-(4-chloro-phenylsulfonylamino)-N-(2-methylmercapto-5-trifluoromethyl-phenyl)-benzamide 53.) 5-Chloro-2-(4-chloro-phenylsulfonylamino)-N-(3-methylsulfonyl-phenyl)-benzamide 54.) 5-Chloro-2-(4-chloro-phenylsulfonylamino)-N-(3-(2-hydroxy-ethylsulfonyl)-phenyl)-benzamide 55.) (4-(5-Chloro-2-(4-chloro-phenylsulfonylamino)-benzoylamino)-phenylmercapto)-acetic acid 56.) 5-Chloro-2-(4-chloro-phenylsulfonylamino)-N-(4-(3,4-dimethyl-isoxazol-5-ylsulfamoyl)-phenyl)-benzamide 57.) 5-Chloro-2-(4-chloro-phenylsulfonylamino)-N-(4-(thiazol-2-ylsulfamoyl)-phenyl)-benzamide 58.) 5-Chloro-2-(3,4-dichloro-phenylsulfonylamino)-N-(4-ethylmercapto-phenyl)-benzamide; M.p.: 171° C.

59.) 2-(4-Chloro-phenylsulfonylamino)-4,5-dimethoxy-N-(4-(thiomorpholine-4-sulfonyl)-phenyl)-benzamide 500 mg (0.95 mmol) of 4-((2-(4-chloro-phenylsulfonylamino)-4,5-dimethoxy-benzoyl)-amino)-benzenesulfonyl fluoride were dissolved in 1 ml of thiomorpholine and heated to 90° C. for 30 min. For working up the mixture was poured onto 50 ml of ice/1 N hydrochloric acid, the precipitate was filtered off with suction, dried in a vacuum-drying chamber over phosphorus pentoxide and recrystallized from hexane/ethyl acetate. 378 mg (65%) of the title compound having a melting point of 241° C. were obtained.

Analogously were obtained:

60.) 2-(4-Chloro-phenylsulfonylamino)-N-(4-(cis-2,6-dimethyl-morpholine-4-sulfonyl)-phenyl)-pyridine-3-carboxamide; M.p.: 256-258° C.

61.) N-(4-(4-Carbamoyl-piperidine-1-sulfonyl)-phenyl)-2-(4-chloro-phenylsulfonylamino)-pyridine-3-carboxamide; M.p.: 273-276° C.

62.) 2-(4-Chloro-phenylsulfonylamino)-N-(4-(piperidine-1-sulfonyl)-phenyl)-pyridine-3-carboxamide; M.p.: 180-183° C.

63.) 5-Chloro-2-(4-chloro-phenylsulfonylamino)-N-(4-(thiomorpholine-4-sulfonyl)-phenyl)-benzamide; M.p.: 246° C.

64.) 5-Chloro-2-(4-chloro-phenylsulfonylamino)-N-(4-(4-methyl-piperazine-1-sulfonyl)-phenyl)-benzamide; M.p.: 219° C.

65.) 5-Chloro-2-(4-chloro-phenylsulfonylamino)-N-(4-(2,6-dimethyl-morpholine-4-sulfonyl)-phenyl)-benzamide; M.p.: 259° C.

66.) 5-Chloro-2-(4-chloro-phenylsulfonylamino)-N-(4-(cis-2,6-dimethyl-morpholine-4-sulfonyl)-phenyl)-benzamide; M.p.: 251° C.

67.) 5-Chloro-2-(4-chloro-phenylsulfonylamino)-N-(4-(4-hydroxy-piperidine-1-sulfonyl)-phenyl)-benzamide; M.p.: 255° C.

68.) 5-Chloro-2-(4-chloro-phenylsulfonylamino)-N-(4-(1,4-dioxa-8-aza-spiro[4.5]decane-8-sulfonyl)-phenyl)-benzamide; M.p.: 256° C.

69.) 5-Chloro-2-(3,4-dichloro-phenylsulfonylamino)-N-(4-(morpholine-4-sulfonyl)-phenyl)-benzamide; M.p.: 253° C.

70.) 5-Chloro-2-(3,4-dichloro-phenylsulfonylamino)-N-(4-(thiomorpholine-4-sulfonyl)-phenyl)-benzamide; M.p.: 222° C.

71.) 5-Chloro-2-(3,4-dichloro-phenylsulfonylamino)-N-(4-(4-methyl-piperazine-1-sulfonyl)-phenyl)-benzamide; M.p.: 246° C.

72.) 2-(4-Chloro-phenylsulfonylamino)4,5-dimethoxy-N-(4-(morpholine-4-sulfonyl)-phenyl)-benzamide; M.p.: 172° C.

73.) 5-Chloro-2-(4-chloro-phenylsulfonylamino)-N-(4-(4-(2-hydroxy-ethyl)-piperazine-1-sulfonyl)-phenyl)-benzamide; M.p.: 277° C.

74.) 2-(4-Chloro-phenylsulfonylamino)-N-(4-(morpholine-4-sulfonyl)-phenyl)-cyclopentanecarboxamide; M.p.: 180° C.

75.) 5-Chloro-2-(4-chloro-phenylsulfonylamino)-N-(4-diethylsulfamoyl-phenyl)-benzamide; M.p.: 226° C.

76.) 5-Chloro-2-(4-chloro-phenylsulfonylamino)-N-(4-(piperidine-1-sulfonyl)-phenyl)-benzamide; M.p.: 240° C.

77.) 5-Chloro-2-(4-chloro-phenylsulfonylamino)-N-(4-(2-methoxy-ethylsulfamoyl)-phenyl)-benzamide; M.p.: 209° C.

78.) 2-(4-Chloro-phenylsulfonylamino)-5-methyl-N-(4-(morpholine-4-sulfonyl)-phenyl)-benzamide; M.p.: 203° C.

79.) 3-(4-Chloro-phenylsulfonylamino)-N-(4-(morpholine-4-sulfonyl)-phenyl)-thiophene-2-carboxamide; M.p.: 220° C.

80.) 3-(4-Chloro-phenysulfonylamino)-N-(4-(morpholine-4-sulfonyl)-phenyl)-1H-pyrazole-4-carboxamide; Oil 81.) 5-Chloro-2-(4-chloro-phenylsulfonylamino)-N-(3-(morpholine-4-sulfonyl)-phenyl)-benzamide; M.p.: 238° C.

82.) 5-Chloro-2-(4-chloro-phenylsulfonylamino)-N-(3-(thiomorpholine-4-sulfonyl)-phenyl)-benzamide; M.p.: 202° C.

83.) 5-Chloro-2-(4-chloro-phenylsulfonylamino)-N-(3-(4-Ethyl-piperazine-1-sulfonyl)-phenyl)-benzamide hydrochloride; M.p.: 245° C.

84.) 3-(4-Chloro-phenylsulfonylamino)-N-(4-(thiomorpholine-4-sulfonyl)-phenyl)-thiophene-2-carboxamide; M.p.: 229° C.

85.) 5-Chloro-2-(4-chloro-phenylsulfonylamino)-N-(4-(morpholine-4-sulfonyl)-phenyl)-benzamide; M.p.: 228° C.

86.) 2-(4-Chloro-phenylsulfonylamino)-5-methyl-N-(4-(thiomorpholine-4-sulfonyl)-phenyl)-benzamide; M.p.: 234° C.

87.) 2-(4-Chloro-phenylsulfonylamino)-4,5-dimethoxy-N-(4-(4-methyl-piperazine-1-sulfonyl)-phenyl)-benzamide; M.p.: 172° C.

88.) 2-(4-Chloro-phenylsulfonylamino)-N-(4-(cis-2,6-dimethyl-morpholine-4-sulfonyl)-phenyl)-4,5-dimethoxy-benzamide; M.p.: 208° C.

89.) 2-(4-Chloro-phenylsulfonylamino)-N-(4-(4-hydroxy-piperidine-1-sulfonyl)-phenyl)-4,5-dimethoxy-benzamide; M.p.: 244° C.

90.) 2-(4-Chloro-phenylsulfonylamino)4,5-dimethoxy-N-(4-(piperidine-3-sulfonyl)-phenyl)-benzamide; M.p.: 258° C.

91.) 2-(4-Chloro-phenylsulfonylamino)-4,5-dimethoxy-N-(4-thiazolidine-3-sulfonyl)-phenyl)-benzamide; M.p.: 261° C.

92.) 2-(4-Chloro-phenylsulfonylamino)-N-(4-(2,5-dihydro-1H-pyrrole-1-sulfonyl)-phenyl)-4,5-dimethoxy-benzamide; M.p.: 262° C.

93.) 2-(4-Chloro-phenylsulfonylamino)-N-(4-(1,2,3,6-tetrahydro-pyridine-1-sulfonyl)-phenyl)-4,5-dimethoxy-benzamide; M.p.: 252° C.

94.) 2-(4-Chloro-phenylsulfonylamino)-4,5-dimethoxy-N-(4-(2-methyl-piperidine-1-sulfonyl)-phenyl)-benzamide; M.p.: 227° C.

95.) 2-(4-Chloro-phenylsulfonylamino)-4,5-dimethoxy-N-(4-(piperazine-1-sulfonyl)-phenyl)-benzamide; M.p.: 243° C.

96.) 4-(4-(2-(4-Chloro-phenylsulfonylamino)-4,5-dimethoxy-benzoylamino)-phenylsulfonyl)-piperazine-1-carboxylic acid ethyl ester; M.p.: 245° C.

97.) 2-(4-Chloro-phenylsulfonylamino)-4,5-dimethoxy-N-(4-(4-methyl-piperidin-1-sulfonyl)-phenyl-benzamide; M.p.: 267° C.

98.) 2-(4-Chloro-phenylsulfonylamino)-4,5-dimethoxy-N-(4-(4-methyl-perhydro-[1,4]diazepine-1-sulfonyl)-phenyl)-benzamide; M.p.: 274° C.

99.) 2-(4-Chloro-phenylsulfonylamino)-N-(4-(4-ethyl-piperazine-1-sulfonyl)-phenyl)-4,5-dimethoxy-benzamide; M.p.: 191° C.

100.) 2-(4-Chloro-phenylsulfonylamino)-N-(4-((2-dimethylamino-ethyl)-ethyl-sulfamoyl)-phenyl)-4,5-dimethoxy-benzamide; M.p.: Dec. >119° C.

101.) 2-(4-Chloro-phenylsulfonylamino)-N-(4-(1,4,5,6-tetrahydro-pyrimidine-1-sulfonyl)-phenyl)-4,5-dimethoxy-benzamide; M.p.: Dec. >237° C.

102.) 2-(4-Chloro-phenylsulfonylamino)-4,5-dimethoxy-N-(4-(4-(pyrimidin-2-yl)-piperazine-1-sulfonyl)-phenyl)-benzamide; M.p.: Dec. >194° C.

103.) 2-(4-Chloro-phenylsulfonylamino)-N-(4-(4-(4-chlorophenyl)-piperazine-1-sulfonyl)-phenyl)-4,5-dimethoxy-benzamide; M.p.: Dec. >243° C.

104.) 2-(4-Chloro-phenylsulfonylamino)-N-(4-(indan-1-yl-sulfamoyl)-phenyl)-4,5-dimethoxy-benzamide; M.p.: 161° C.

105.) 2-(4-Chloro-phenylsulfonylamino)-N-(4-((2-(1H-indol-3-yl)-ethyl)-methyl-sulfamoyl)-phenyl)-4,5-dimethoxy-benzamide; M.p.: 182° C.

106.) 1-(4-((2-(4-Chloro-phenylsulfonylamino)-4,5-dimethoxy-benzoyl)-amino)-phenylsulfonyl)-piperidine-4-carboxamide; M.p.: 252° C.

107.) 2-(4-Chloro-phenylsulfonylamino)-N-(4-cyclopropylsulfamoyl-phenyl)-4,5-dimethoxy-benzamide; M.p.: 222° C.

108.) 2-(4-Chloro-phenylsulfonylamino)-N-(4-(3-hydroxy-pyrrolidine-1-sulfonyl)-phenyl)-4,5-dimethoxy-benzamide; M.p.: 272° C.

109.) N-(4-(Allyl-cyclohexyl-sulfamoyl)-phenyl)-2-(4-chloro-phenylsulfonylamino)-4,5-dimethoxy-benzamide; M.p.: 182° C.

110.) 1-(4-((2-(4-Chloro-phenylsulfonylamino)-4,5-dimethoxy-benzoyl)-amino)-phenylsulfonyl)-pyrrolidine-2-carboxylic acid; M.p.: 240° C. (sintering)

111.) 5-Chloro-2-nitro-benzoyl chloride 100.00 g (0.50 mol) of 5-chloro-2-nitrobenzoic acid were mixed with 72.20 g (0.61 mol) of thionyl chloride and the mixture was heated under reflux for 2 h. The excess thionyl chloride was removed in vacuo. 106.50 g (ca. 98%) of crude 5-chloro-2-nitro-benzoyl chloride were obtained as an oil.

Analogously was obtained:

112.) 5-Methyl-2-nitro-benzoyl chloride; Oil

113.) 4-(5-Chloro-2-nitro-benzoylamino)-benzenesulfonyl fluoride 86.00 g (0.39 mol) of 5-chloro-2-nitro-benzoyl chloride was dissolved in 300 ml of toluene, a solution of 62.00 g (0.35 mol) of 4-aminobenzenesulfonyl fluoride was added dropwise, and the mixture was heated under reflux for 4 h. Subsequently it was cooled, concentrated in vacuo to half of its volume, cooled, and the precipitated solid was filtered off with suction. 121.60 g (86%) of the title compound having a melting point of 182-184° C. were obtained.

Analogously were obtained:

114.) 4-(5-Methyl-2-nitro-benzoylamino)-benzenesulfonyl fluoride; M.p.: 179° C.

115.) 5-Chloro-N-(4-ethylmercapto-phenyl)-2-nitro-benzamide

116.) 5-Chloro-N-(4-(morpholine-4-sulfonyl)-phenyl)-2-nitro-benzamide 120.00 g (0.33 mol) of 4-(5-chloro-2-nitro-benzoylamino)-benzenesulfonyl fluoride, 29.10 g (0.33 mol) of morpholine and 33.85 g (0.33 mol) of triethylamine were stirred in 1200 ml of toluene at 60° C. for 2 days. The precipitated solid was filtered off with suction and recrystallized from acetone/n-hexane. 102.10 g (71%) of the title compound having a melting point of 243-245° C. were obtained.

Analogously were obtained:

117.) 5-Chloro-2-nitro-N-(4-(thiomorpholine-4-sulfonyl)-phenyl)-benzamide; M.p.: 120° C.

118.) 5-Methyl-N-(4-(morpholine-4-sulfonyl)-phenyl)-2-nitro-benzamide; M.p.: 249° C.

119.) N-(4-(Morpholine-4-sulfonyl)-phenyl)-5-(morpholin-4-yl)-2-nitro-benzamide 20.00 g (0.56 mol) of 4-(5-chloro-2-nitro-benzoylamino)-benzenesulfonyl fluoride in 48.5 g (0.557 mol) of morpholine were heated under reflux for 1 h. Subsequently the mixture was cooled, poured onto ice/hydrochloric acid and filtered with suction. 26.0 g (98%) of the title compound having a melting point of 252° C. were obtained.

120.) 2-Amino-5-chloro-N-(4-(morpholine-4-sulfonyl)-phenyl)-benzamide 11.10 g (26.1 mmol) of 5-chloro-N-(4-(morpholine-4-sulfonyl)-phenyl)-2-nitro-benzamide were dissolved in 440 ml of tetrahydrofuran/methanol (1:1) and a solution of 27.23 g (156.4 mmol) of sodium dithionite in 330 ml of water was added dropwise. After stirring for 1 h at room temperature the organic solvents were removed in rotary evaporator, and the precipitated product was filtered off with suction and purified by chromatography over silica with methylene chloride/methanol (9:1). 5.68 g (55%) of the title compound having a melting point of 229-231° C. were obtained.

Analogously were obtained:

121.) 2-Amino-5-chloro-N-(4-(thiomorpholine-4-sulfonyl)-phenyl)-benzamide; M.p.: 177° C.

122.) 2-Amino-N-(4-(morpholine-4-sulfonyl)-phenyl)-(5-morpholin-4-yl)-benzamide; M.p.: 228° C.

123.) 2-Amino-5-chloro-N-(4-ethylsulfonyl-phenyl)-benzamide; M.p.: 159-161° C.

124.) 5-Chloro-2-(5-chloro-1,3-dimethyl-1H-pyrazole-4-sulfonyl-amino)-N-(4-(thiomorpholine-4-sulfonylyphenyl)-benzamide 250 mg (0.60 mmol) of 2-amino-5-chloro-N-(4-(thiomorpholine-4-sulfonyl)-phenyl)-benzamide were dissolved in 10 ml of dry pyridine, and a solution of 195 mg (0.85 mmol) 5-chloro-1,3-dimethyl-1H-pyrazole-4-sulfonyl chloride in 5 ml of pyridine was added dropwise at 0° C. After 2 h the mixture was poured onto ice, the precipitated solid was filtered off with suction and purified by chromatography over silica with methylene chloride/methanol (98:2). 250 mg (69%) of the title compound having a melting point of 215-216° C. were obtained.

Analogously were obtained:

125.) 5-Chloro-N-(4-(morpholine-4-sulfonyl)-phenyl)-2-(4-methyl-phenylsulfonylamino)-benzamide; M.p.: 214° C.

126.) 5-Chloro-2-(3,4-dimethoxy-phenylsulfonylamino)-N-(4-(morpholine-4-sulfonyl)-phenyl)-benzamide; M.p.: 245° C.

127.) 5-Chloro-N-(4-(morpholine-4-sulfonyl)-phenyl)-2-(4-trifluoromethoxy-phenylsulfonylamino)-benzamide; M.p.: 195° C.

128.) 2-((4-Acetylamino-phenyl)-sulfonylamino)-5-chloro-N-(4-(morpholine-4-sulfonyl)-phenyl)-benzamide; M.p.: 198° C.

129.) 5-Chloro-2-(5-chloro-thiophene-2-sulfonylamino)-N-(4-(morpholine-4-sulfonyl)-phenyl)-benzamide; M.p.: 112° C.

130.) 5-Chloro-2-(5-chloro-1,3-dimethyl-pyrazole-4-sulfonyl-amino)-N-(4-(morpholine-4-sulfonyl)-phenyl)-benzamide; M.p.: 161° C.

131.) 5-Chloro-2-((1-methyl-imidazole-4-sulfonyl)-amino)-N-(4-(morpholine-4-sulfonyl)-phenyl)-benzamide; M.p.: 141° C.

132.) 5-Chloro-N-(4-(morpholine-4-sulfonyl)-phenyl)-2-(pyridine-3-sulfonylamino)-benzamide; M.p.: 222° C.

133.) 2-(4-Benzoyloxy-phenylsulfonylamino)-5-chloro-N-(4-(morpholine-4-sulfonyl)-phenyl)-benzamide; M.p.: 245° C.

134.) 5-Chloro-2-(ethylsulfonylamino)-N-(4-(morpholine-4-sulfonyl)-phenyl)-benzamide; M.p.: 274-276° C.

135.) 2-((2-Acetamido-4-methyl-thiazole-5-sulfonyl)-amino)-5-chloro-N-(4-(morpholine-4-sulfonyl)-phenyl)-benzamide; M.p.: 257° C.

136.) 5-Chloro-N-(4-(morpholine-4-sulfonyl)-phenyl)-2-(thiophene-2-sulfonylamino)-benzamide; M.p.: 216° C.

137.) 5-Chloro-N-(4-(morpholine-4-sulfonyl)-phenyl)-2-(4-trifluoromethyl-phenylsulfonylamino)-benzamide; M.p.: 264° C.

138.) 2-(4-Bromo-phenylsulfonylamino)-5-chloro-N-(4-(morpholine-4-sulfonyl)-phenyl)-benzamide; M.p.: 232° C.

139.) 2-(3,5-Bis-trifluoromethyl-phenylsulfonylamino)-5-chloro-N-(4-(morpholine-4-sulfonyl)-phenyl)-benzamide; M.p.: 209° C.

140.) 5-Chloro-N-(4-(morpholine-4-sulfonyl)-phenyl)-2-(4-nitro-phenylsulfonylamino)-benzamide; M.p.: 239° C.

141.) 5-Chloro-2-(4-cyano-phenylsulfonylamino)-N-(4-(morpholine-4-sulfonyl)phenyl)-benzamide; M.p.: 238° C.

142.) 5-Chloro-2-(4-methylsulfonyl-phenylsulfonylamino)-N-(4-(morpholine-4-sulfonyly)-phenyl)-benzamide; M.p.: 181° C.

143.) 5-Chloro-2-(4-isopropyl-phenylsulfonylamino)-N-(4-(morpholine-4-sulfonyl)-phenyl)-benzamide; M.p.: 105° C.

144.) 5-Chloro-N-(4-(morpholine-4-sulfonyl)-phenyl)-2-((2-phenyl-ethenyl)-sulfonylamino)-benzamide; M.p.: 278° C. 145.) 5-Chloro-2-(4,5-dibromo-thiophene-2-sulfonylamino)-N-(4-(morpholine-4-sulfonyl)-phenyl)-benzamide; M.p.: 232° C.

146.) 5-Chloro-2-(4-fluoro-phenylsulfonylamino)-N-(4-(morpholine-4-sulfonyl)-phenyl)-benzamide; M.p.: 245° C.

147.) 5-Chloro-N-(4-(morpholine-4-sulfonyl)-phenyl)-2-(5-phenylsulfonyl-thiophene-2-sulfonylamino)-benzamide; M.p.: 103° C.

148.) 5-Chloro-2-(3-chloro-4-methoxy-phenylsulfonylamino)-N-(4-(morpholine-4-sulfonyl)-phenyl)-benzamide; M.p.: 274° C.

149.) 5-Chloro-N-(4-(morpholine-4-sulfonyl)-phenyl)-2-(quinoline-8-sulfonylamino)-benzamide; M.p.: 262° C.

150.) 5-Chloro-N-(4-(morpholine-4-sulfonyl)-phenyl)-2-(2,4,6-trimethyl-phenylsulfonylamino)-benzamide; M.p.: 240° C.

151.) 5-Chloro-N-(4-(morpholine-4-sulfonyl)-phenyl)-2-(3-nitro-phenylsulfonylamino)-benzamide; M.p.: 220° C.

152.) 5-Chloro-2-(4-methoxy-phenylsulfonylamino)-N-(4-(morpholine-4-sulfonyl)-phenyl)-benzamide; M.p.: 269° C.

153.) 5-Chloro-2-methylsulfonylamino-N-(4-(morpholine-4-sulfonyl)-phenyl)-benzamide; M.p.: 248° C.

154.) 5-Chloro-N-(4-(morpholine-4-sulfonyl)-phenyl)-2-phenylmethylsulfonylamino-benzamide; M.p.: 106° C.

155.) 5-Chloro-N-(4-(morpholine-4-sulfonyl)-phenyl)-2-(2,2,2-trifluoro-ethylsulfonylamino)-benzamide; M.p.: 208° C.

156.) 2-(Butyl-sulfonylamino)-5-chloro-N-(4-(morpholine-4-sulfonyl)-phenyl)-benzamide; M.p.: 102° C.

157.) 5-Chloro-N-(4-(morpholine-4-sulfonyl)-phenyl)-2-(3-trifluoromethyl-phenylsulfonylamino)-benzamide; M.p.: 212° C.

158.) 2-(4-Bromo-2,5-dichloro-thiophene-3-sulfonylamino)-5-chloro-N-(4-(morpholine-4-sulfonyl)-phenyl)-benzamide; M.p.: 267° C.

159.) 5-Chloro-N-(4-(morpholine-4-sulfonyl)-phenyl)-2-(2-triflubromethyl-phenylsulfonylamino)-benzamide; M.p.: 234° C.

160.) 5-Chloro-2-(3-chloro-phenylsulfonylamino)-N-(4-(morpholine-4-sulfonyl)-phenyl)-benzamide; M.p.: 206° C.

161.) 2-(4-Bromo-2-methoxy-phenylsulfonylamino)-5-chloro-N-(4-(morpholine-4-sulfonyl)-phenyl)-benzamide; M.p.: 260° C.

162.) 5-Chloro-2-(2,6-dichloro-phenylsulfonylamino)-N-(4-(morpholine-4-sulfonyl)-phenyl)-benzamide; M.p.: 244° C.

163.) 5-Chloro-2-(2-cyano-phenylsulfonylamino)-N-(4-(morpholine-4-sulfonyl)-phenyl)-benzamide; M.p.: 200° C.

164.) 2-(4-Butoxy-phenylsulfonylamino)-5-chloro-N-(4-(morpholine-4-sulfonyl)-phenyl)-benzamide; M.p.: 225° C.

165.) 5-Chloro-2-(7,7-dimethyl-2-oxo-bicyclo[2.2.1]heptane-1-sulfonylamino)-N-(4-(morpholine-4-sulfonyl)-phenyl)-benzamide; M.p.: 120° C.

166.) 5-Chloro-2-(3-fluoro-phenylsulfonylamino)-N-(4-(morpholine-4-sulfonyl)-phenyl)-benzamide; M.p.: 204° C.

167.) 2-(4-Chloro-phenylsulfonylamino)-N-(4-(morpholine-4-sulfonyl)-phenyl)-5-(morpholin-4-yl)-benzamide; M.p.: 264° C.

168.) 5-Chloro-N-(4-ethylsulfonyl-phenyl)-2-(4-methyl-phenylsulfonylamino)-benzamide; M.p.: 188-192° C.

169.) 5-Chloro-2-(5-chloro-thiophene-2-sulfonylamino)-N-(4-ethylsulfonyl-phenyl)-benzamide; M.p.: 195-197° C.

170.) 5-Chloro-2-(4-chloro-3-nitro-phenylsulfonylamino)-N-(4-ethylsulfonyl-phenyl)-benzamide; M.p.: 196-198° C.

171.) 5-Chloro-2-(4-chloro-phenylsulfonylamino)-N-(4-ethylsulfonyl-phenyl)-benzamide; M.p.: 180-185° C.

172.) 5-Chloro-2-(3,5-dimethyl-isoxazole-4-sulfonylamino)-N-(4-ethylsulfonyl-phenyl)-benzamide; M.p.: Dec. >249° C.

173.) 5-Chloro-2-ethylsulfonylamino-N-(4-ethylsulfonyl-phenyl)-benzamide; M.p.: 103° C.

174.) 4-Chloro-N-(2-(1H-benzimidazol-2-yl)-4-chloro-phenyl)-benzenesulfonamide 1.00 g (2.7 mmol) of 5-chloro-2-(4-chloro-phenylsulfonylamino)-benzoyl chloride and 296 mg (2.7 mmol) of o-phenylenediamine in 150 ml of toluene were heated under reflux for 1 h. A small amount of solid was filtered off with suction and the filtrate was evaporated. The residue was taken up in 50 ml of toluene, 600 mg of thionyl chloride were added and the mixture was again heated under reflux for 10 h. Subsequently it was cooled and the precipitated solid was filtered off with suction. 280 mg (25%) of the title compound having a melting point of 225-228° C. were obtained.

175.) 2-(4-Chloro-phenylsulfonylamino)-4,5-dimethoxy-N-(4-(1,1-dioxo-thiomorpholine-4-sulfonyl)-phenyl)-benzamide and 176.) 2-(4-Chloro-phenylsulfonylamino)-4,5-dimethoxy-N-(4-(1-oxo-thiomorpholine-4-sulfonyl)-phenyl)-benzamide 500 mg (0.82 mmol) of 2-(4-chloro-phenylsulfonylamino)-4,5-dimethoxy-N-(4-(thiomorpholine-4-sulfonyl)-phenyl)-benzamide in 50 ml of acetone were cooled to 0° C. A solution of 371 mg (1.23 mmol) of 57% m-chloroperbenzoic acid in 20 ml of acetone was added and the mixture was stirred at room temperature over night. For working up it was poured onto water/ice and the precipitate was filtered off with suction. The two products obtained as a mixture were separated by chromatography over silica with methylene chloride/methanol (97:3).

Analogously were obtained:

177.) 5-Chloro-2-(4-chloro-phenylsulfonylamino)-N-(4-(1,1-dioxo-thiomorpholine-4-sulfonyl)-phenyl)-benzamide; M.p.: 182° C.

178.) 5-Chloro-2-(4-chloro-phenylsulfonylamino)-N-(4-(1-oxo-thiomorpholine-4-sulfonyl)-phenyl)-benzamide; M.p.: 233° C.

179.) 5-Chloro-2-(3,4-dichloro-phenylsulfonylamino)-N-(4-ethylsulfonyl-phenyl)-benzamide; M.p.: 240° C.

180.) 5-Chloro-N-(4-ethylsulfonyl-phenyl)-2-nitro-benzamide

181.) 4-Chloro-N-(4-chloro-2-(6-(morpholine-4-sulfonyl)-1H-benzimidazol-2-yl)-phenyl)-benzenesulfonamide 200 mg (0.5 mmol) of 4-chloro-N-(2-(1H-benzimidazol-2-yl)-4-chloro-phenyl)-benzenesulfonamide were added at 0° C. to 1 ml of chlorosulfuric acid and heated to 60° C. for 30 min. Subsequently the mixture was poured onto water/ice, and the solid was filtered off with suction, dried and added at 0° C. to 1 ml of morpholine. After stirring at room temperature for 1 h the mixture was poured onto ice/hydrochloric acid and extracted with ethyl acetate. The extracts were evaporated and the residue was purified by chromatography over silica with hexane/ethyl acetate (1:1). 20 mg (7%) of the title compound having a melting point of 225-228° C. were obtained.

H-NMR ($D_6$-DMSO): δ (ppm)=2.9 (m, 4 H, morpholine-H), 3.6 (m, 4 H, morpholine-H), 7.5 (dd, 4 H, phenylene-H), 7.4-8.2 (m, 6 H, benzo-H, phenyl-H)

182.) 5-Chloro-N-(4-(morpholine-4-sulfonyl)-phenyl)-2-(2-(pyrrolidin-1-yl)-ethylsulfonylamino)-benzamide The compound was prepared by using 2-chloro-ethylsulfonyl chloride. The 1-(2-(4-chloro-2-(4-(morpholine-4-sulfonyl)-phenylcarbamoyl)-phenylsulfamoyl)-ethyl)-pyridinium chloride that was isolated as an intermediate was reacted with pyrrolidine to give the title compound.

$^1$H-NMR ($D_6$-DMSO): δ (ppm) 1.8 (m, 4 H, pyrrolidine-H), 2.65 (m, 4 H, pyrrolidine-H), 3.0 (m, 4 H, morpholine-H), 3.1 (t, 2 H, ethylene-H), 3.35 (t, 2 H, ethylene-H), 3.75 (m, 4 H, morpholine-H), 7.50 (dd, 1 H, H-4), 7.7 (d, 1 H, H-3), 7.75 (dd, 1 H, H-6), 7.85 ("dd", 4 H, phenylene-H).

183.) 5-Chloro-2-(4-chloro-phenylsulfonylamino)-N-(4-isopropylmercapto-phenyl)-benzamide 1.00 g (2.21 mmol) of 5-chloro-2-(4-chloro-phenylsulfonylamino)-N-(4-mercapto-phenyl)-benzamide were dissolved in 25 ml of dimethylformamide and 0.25 g (2.21 mmol) of potassium tert-butylate were added. The mixture was stirred at room temperature for 15 min, then 0.27 g (2.21 mmol) of isopropyl bromide were added dropwise, and the mixture was heated to 60° C. for 8 h. For working up it was poured onto water and extracted with ethyl acetate. The combined extracts were evaporated and the residue was purified by chromatography over silica with hexane/ethyl acetate (3:1). 420 mg (39%) of the title compound having a melting point of 168-169° C. were obtained.

Analogously were obtained:

184.) 5-Chloro-2-(4-chloro-phenylsulfonylamino)-N-(4-cyanomethylmercapto-phenyl)-benzamide; M.p.: 104° C.

185.) (4-((5-Chloro-2-(4-chloro-phenylsulfonylamino)-benzoyl)-amino)-phenylmercapto)-acetic acid ethyl ester; M.p.: 133° C.

186.) 5-Chloro-2-(4-chloro-phenylsulfonylamino)-N-(4-(2-(morpholin-4-yl)-ethylmercapto)-phenyl)-benzamide; M.p.: 95° C.

187.) 5-Chloro-2-(4-chloro-phenylsulfonylamino)-N-(4-(2-(2-methoxy-ethoxyy)-ethylmercapto)-phenyl)-benzamide; Oil 188.) 5-Chloro-2-(4-chloro-phenylsulfonylamino)-N-(4-(prop-2-inyl)-mercapto-phenyl)-benzamide; M.p.: 185° C.

189.) 5-Chloro-2-(4-chloro-phenylsulfonylamino)-N-(4-isopropylmercapto-phenyl)-benzamide; M.p.: 169° C.

190.) 5-Chloro-2-(5-chloro-thiophene-2-sulfonylamino)-N-(4-(morpholine-4-sulfonyl)-phenyl)-benzamide sodium salt A mixture of 0.48 g finely powdered sodium hydroxide and 7 g of 5-chloro-2-(5-chloro-thiophene-2-sulfonylamino)-N-(4-(morpholine-4-sulfonyl)-phenyl)-benzamide in 250 ml of ethanol was brought into solution by short heating. Then the mixture was evaporated in vacuo, 50 ml of water were added and it was again evaporated in vacuo to dryness. This procedure was repeated twice. The resulting product was dried in vacuo at 50° C. M.p.: 343° C. (Dec.)

Analogously to the above compounds the following example compounds were obtained:

191.) 4,5-Dimethoxy-2-(5-chloro-thiophene-2-sulfonylamino)-N-(4-(N-methyl-N-(pyridin-3-yl-methyl)-aminosulfonyl)-phenyl)-benzamide hydrochloride; M.p.: 214° C.

192.) 5-Chloro-2-(4-chloro-phenylsulfonylamino)-N-(4-(morpholine-4-sulfonyl)-3-methyl-phenyl)-benzamide; M.p.: 192° C.

193.) 5-Chloro-2-(4-chloro-phenylsulfonylamino)-N-(4-(cis-2,6-dimethyl-morpholine-4-sulfonyl)-3-methyl-phenyl)-benzamide; M.p.: 254° C.

194.) 5-Chloro-2-(4-chloro-phenylsulfonylamino)-N-(4-(3,5-dimethyl-piperidine-1-sulfonyl)-3-methyl-phenyl)-benzamide; M.p.: 242° C.

195.) 5-Chloro-2-(4-chloro-phenylsulfonylamino)-N-(4-(piperidine-1-sulfonyl)-3-methyl-phenyl)-benzamide; M.p.: 189° C.

196.) 4,5-Dimethoxy-2-(3,5-dimethyl-isoxazole-4-sulfonylamino)-N-(4-(N-methyl-N-(pyridin-3-yl-methyl)-aminosulfonyl)-phenyl)-benzamide; M.p.: 213° C.

197.) 4,5-Dimethoxy-2-(3,5-dimethyl-isoxazole-4-sulfonylamino)-N-(4-(N-(pyridin-3-yl-methyl)-aminosulfonyl)-phenyl)-benzamide; M.p.: 216° C.

198.) 5-Chloro-2-(2,4-dimethyl-thiazole-5-sulfonylamino)-N-(4-(morpholine-4-sulfonyl)-phenyl)-benzamide; M.p.: 190° C.

199.) 4,5-Dimethoxy-2-(4-chloro-phenylsulfonylamino)-N-(4-(3,5-dimethyl-piperidine-1-sulfonyl)-phenyl)-bezamide; M.p.: 249° C. (Dec.)

200.) 2-(4-Chloro-phenylsulfonylamino)-N-(4-(N-methyl-N-(pyridin-3-yl-methyl)-aminosulfonyl)-phenyl)-benzamide; Resin 201.) 3,4-Dimethoxy-2-(4-chloro-pheny,sulfonylamino)-N-(4-(N-methyl-N-(pyridin-3-yl-methyl)-aminosulfonyl)-phenyl)-benzamide; M.p.: 241° C.

202.) 5-Bromo-2-(5-chloro-thiophene-2-sulfonylamino)-N-(4-(morpholine-4-sulfonyl)-3-methyl-phenyl)-benzamide; M.p.: 249° C.

203.) 5-Bromo-2-(5-chloro-thiophene-2-sulfonylamino)-N-(4-(cis-2,6-dimethyl-morpholine-4-sulfonyl)-phenyl)-benzamide; M.p.: 244° C. 204.) 5-Bromo-2-(5-chloro-thiophene-2-sulfonylamino)-N-(4-(thiomorpholine-4-sulfonyl)-phenyl)-benzamide; M.p.: 197° C.

205.) 4,5-Dimethoxy-2-(5-chloro-thiophene-2-sulfonylamino)-N-(4-(1,2,3,4-tetrahydro-isoquinoline-2-sulfonyl)-phenyl)-benzamide; M.p.: 213° C.

206.) 4,5-Dimethoxy-2-(5-chloro-thiophene-2-sulfonylamino)-N-(4-(thiomorpholine-4-sulfonyl)-phenyl)-benzamide; M.p.: 232° C.

207.) 4,5-Dimethoxy-2-(5-chloro-thiophene-2-sulfonylamino)-N-(4-(cis-2,6-dimethylpiperidine-1-sulfonyl)-phenyl)-benzamide; M.p.: 213° C.

208.) 5-Chloro-2-(3,5-dimethyl-isoxazole-4-sulfonylamino)-N-(4-(1,2,3,4-tetrahydroisoquinoline-2-sulfonyl)-phenyl)-benzamide; M.p.: 260° C.

209.) 5-Chloro-2-(3,5-dimethyl-isoxazole-4-sulfonylamino)-N-(4-(N-methyl-N-(pyridin-3-yl-methyl)-aminosulfony)-phenyl)-benzamide; M.p.: 65° C. (sintering)

210.) 6-Methyl-2-(4-chloro-phenylsulfonylamino)-N-(4-(perhydroazepine-1-sulfonyl)-phenyl)-benzamide; M.p.: 151° C.

211.) 6-Chloro-2-(4-chloro-phenylsulfonylamino)-N-(4-(pyrrolidine-1-sulfonyl)-phenyl)-benzamide; M.p.: 217° C.

212.) 6-Chloro-2-(4-chloro-phenylsulfonylamino)-N-(4-(4-hydroxybutylamino)-sulfonyl)-phenyl)-benzamide; Resin 213.) 5-Chloro-2-(4-chloro-phenylsulfonylamino)-N-(4-(N-ethyl-N-(pyridin-4-yl-methyl)-aminosulfonyl)-phenyl)-benzamide; Resin 214.) 2-(4-Chloro-phenylsulfonylamino)-N-(4-thiomorpholine-4-sulfonyl)-phenyl)-benzamide; M.p.: 209° C.

215.) 3-Methyl-2-(4-chloro-phenylsulfonylamino)-N-(4-(N-methyl-N-(2-(pyridin-2-yl)-ethyl)-aminosulfonyl)-phenyl)-benzamide; M.p.: 193° C.

216.) 4,5-Difluoro-2-(4-chloro-phenylsulfonylamino)-N-(4-(4-aminocarbonyl-piperidine-1-sulfonyl)-phenyl)-benzamide; M.p.: 227° C.

217.) 4,5-Difluoro-2-(4-chloro-phenylsulfonylamino)-N-(4-(4-(2-hydroxyethyl)-piperazine-1-sulfonyl)-phenyl)-benzamide; Resin 218.) 5-Chloro-4-methoxy-2-(5-chloro-thiophene-2-sulfonylamino)-N-(4-(morpholine-4-sulfonyl)-phenyl)-benzamide; Oil 219.) 5-Chloro-4-methoxy-2-(5-chloro-thiophene-2-sulfonylamino)-N-(4-(cis-2,6-dimethyl-morpholine-1-sulfonyl)-phenyl)-benzamide; M.p.: 89° C.

220.) 5-Chloro-4-methoxy-2-(5-chloro-thiophene-2-sulfonylamino)-N-(4-(N-pyridin-3-yl)-N-methyl-aminosulfonyl)-phenyl)-benzamide; M.p.: 135° C.

221.) 4,5-Dimethoxy-2-(4-chloro-phenylsulfonylamino)-N-(4-(cis-2,6-dimethyl-morpholine-4-sulfonyl)-phenyl)-benzamide sodium salt; M.p.: 330° C. (Dec)

222.) 5-Chloro-2-(3,5-dimethyl-isoxazole-4-sulfonylamino)-N-(4-(cis-2,6-dimethyl-morpholine-4-sulfonyl)-phenyl)-benzamide; M.p.: 230° C.

223.) 5-Chloro-2-(3,5-dimethyl-isoxazole-4-sulfonylamino)-N-(4-(3,5-dimethylpiperidine-1-sulfonyl)-phenyl)-benzamide; M.p.: 61° C.

224.) 5-Chloro-2-(3,5-dimethyl-isoxazole-4-sulfonylamino)-N-(4-(morpholine-4-sulfonyl)-phenyl)-benzamide; M.p.: 286° C.

225.) 5-Chloro-2-(5-chloro-thiophene-2-sulfonylamino)-N-(4-phenylsulfonyl)-phenyl)-benzamide; M.p.: 227° C.

226.) 4-Chloro-2-(4-chloro-phenylsulfonylamino)-N-(4-(cis-2,6-dimethyl-morpholine-4-sulfonyl)-phenyl-benzamide; M.p.: 103° C.

Pharmacological Investigations (1) Activation of the Soluble Quanylate Cyclase

The activation of the soluble guanylate cyclase (sGC) which catalyzes the conversion of guanosine triphosphate (GTP) into cyclic guanosine monophosphate (cGMP) and pyrophosphate, by the compounds according to the invention was quantified with the aid of an enzyme immunoassay (EIA) from Amersham. For this purpose the substances to be tested were initially incubated with sGC in microtiter plates, and the amount of the cGMP formed was then determined.

The sGC which was employed had been isolated from bovine lung (see Methods in Enzymology, Volume 195, p. 377). The test solutions (100 µl per well) contained 50 mM triethanolamine (TEA) buffer (pH 7.5), 3 mM $MgCl_2$, 3 mM reduced glutathione (GSH), 0.1 mM GTP, 1 mM 3-isobutyl-1-methylxanthine (IBMX), suitably diluted enzyme solution and the substance to be tested or, in the control experiments, the solvent. The substances to be tested were dissolved in dimethyl sulfoxide (DMSO) and the solution was diluted with DMSO/water, so that the final concentration (c) of the substance to be tested in the test solution had the value indicated in the table. The DMSO concentration in the test solution was 5% (v/v). The reaction was initiated by addition of the sGC. The reaction mixture was incubated at 37° C. for 15 to 20 minutes and then stopped by ice-cooling and addition of the stop reagent (50 mM EDTA, pH 8.0). An aliquot of 50 µl was taken and used for determining the cGMP content using the acetylation protocol of the Amersham cGMP-EIA kit. The absorption of the samples was measured at 450 nm (reference wavelength 620 nm) in a microtiter plate reader. The cGMP concentration was determined using a standard curve which was obtained under the same test conditions. The activation of sGC by a test substance is given as the n-fold stimulation of the basal enzyme activity which was found in the control experiments (using solvent instead of test substance) (calculated using the formula n-fold stimulation=$[cGMP]_{test\ substance}/[cGMP]_{control}$).

The following results were obtained:

| Compound of Example No. | Concentration "c" [µM] | "n-fold" stimulation |
| --- | --- | --- |
| 23 | 50 | 14.7 |
| 59 | 50 | 34.8 |
| 63 | 50 | 33.9 |
| 64 | 50 | 23.9 |
| 65 | 50 | 24.6 |
| 66 | 50 | 33 |
| 67 | 50 | 29.6 |
| 68 | 50 | 12.1 |
| 69 | 50 | 28.3 |
| 70 | 50 | 25.1 |
| 71 | 50 | 13.4 |
| 72 | 50 | 27 |
| 73 | 50 | 16.5 |
| 75 | 50 | 5.1 |
| 76 | 50 | 10.6 |
| 77 | 50 | 5.9 |
| 79 | 50 | 15.4 |
| 84 | 50 | 23.7 |
| 86 | 50 | 32.9 |
| 87 | 50 | 12.5 |
| 88 | 50 | 24.4 |
| 89 | 50 | 11.6 |
| 124 | 50 | 31.2 |
| 129 | 50 | 8.6 |
| 130 | 50 | 35.3 |
| 132 | 50 | 9.9 |
| 134 | 50 | 7.2 |
| 136 | 50 | 24.2 |
| 137 | 50 | 4.6 |
| 139 | 50 | 21.9 |
| 145 | 50 | 8 |
| 146 | 50 | 10.2 |
| 148 | 50 | 15.5 |
| 150 | 50 | 15.3 |
| 151 | 50 | 19.9 |
| 155 | 50 | 7.8 |
| 156 | 50 | 7.8 |
| 157 | 50 | 4.6 |
| 175 | 50 | 21.1 |
| 176 | 50 | 13.9 |
| 191 | 10 | 27.5 |
| 192 | 10 | 26.7 |
| 193 | 10 | 31.1 |
| 194 | 5 | 20.0 |
| 195 | 10 | 16.2 |
| 196 | 10 | 21.9 |
| 206 | 50 | 19.3 |
| 208 | 10 | 23.1 |
| 209 | 10 | 28.5 |
| 222 | 10 | 29.5 |
| 223 | 10 | 27.1 |
| 224 | 50 | 27.8 |
| 225 | 10 | 13.4 |
| 226 | 25 | 3.3 |

(2) Relaxation of Rat Aorta

For this test, normotensive male Wistar-Kyoto rats were sacrificed by a blow to the neck. The abdominal cavity and the thorax were opened by a medium sternotomy. The descending aorta was subsequently removed, freed of connective tissue and divided into 8 rings of a length of approximately 4 mm. The tip of a pair of tweezers was introduced into the lumen of 4 of the 8 rings. The endothelium was removed by carefully rolling the rings over the tip of the pair of tweezers. All 8 aorta rings (4 with endothelium and 4 without endothelium) were subsequently suspended in an organ bath (Schuler-Organbad; Hugo Sachs Elektronik) at a constant temperature of 37° C. for the isometric determination of the contractile tone. For 30 minutes, the rings were calibrated at a resting tension of 1 g in carbonated (95% $O_2$; 5% $CO_2$) Krebs-Henseleit solution (composition: $Na^+$ 144.0 mM; $K^+$ 5.9 mM; $Cl^-$ 126.9 mM; $Ca^{2+}$ 1.6 mM; $Mg^{2+}$ 1.2 mM; $H_2PO_4^-$ 1.2 mM; $SO_4^{2-}$ 1.2 mM; $HCO_3^-$ 25.0 mM; D-glucose 11.1 mM) of pH 7.4. Additionally, 1 µmol/l of indomethacin were added to the Krebs-Henseleit solution to inhibit prostaglandin biosynthesis. The rings were subsequently precontracted by addition of phenylephrine (concentration in the solution: 1 µM) and the endothelium-dependent relaxation or the functional loss of the endothelium was tested by addition of acetylcholine (concentration in the solution: 1 µM). After a 30-minute washing period, the rings were then again precontracted by addition of phenylephrine (1 μM), and the relaxing action of the test substances of the formula I was determined by administration of cumulative doses of the latter. The data were evaluated by standard methods. Given is the concentration $IC_{50}$ by which contraction is inhibited by 50% (50% relaxation).

The following results were obtained:

| Compound of Example No. | | $IC_{50}$ |
|---|---|---|
| 59 | ring without endothelium | 0.27 μM |
| 59 | ring with endothelium | 0.52 μM |
| 88 | ring without endothelium | 0.29 μM |
| 88 | ring with endothelium | 0.67 μM |
| 129 | ring without endothelium | 0.31 μM |
| 129 | ring with endothelium | 0.46 μM |

(3) Hemodynamic Effect in the Pig

Three pigs (German landrace) were anesthetized (Ketamine 20 mg/kg i.m., Methomidate 8 mg/kg i.p., Xylazine 2.5 mg/kg i.m. and Pentobarbital 25 mg/kg i.v. as a bolus plus 0.16 mg/kg per minute). The trachea was intubated and the animals were given artificial respiration with air. Oxygen was added to keep the blood gas parameters in the normal range. To record the blood pressure (BP; BP(s) =systolic blood pressure, BP(d)=diastolic blood pressure) by means of a Statham 23 Db pressure transducer a catheter was inserted into the right A. Femoralis. The left ventricular pressure (LVP), the left ventricular end-diastolic pressure (LVEDP), the contractility (dP/dt) and the heart rate (HR) were determined with a Millar PC 350 catheter "tip manometer" which was inserted into the right ventricle. After a stabilization period of the hemodynamic parameters of 30 minutes the test substance was administered in the indicated dose into the exposed duodenum by means of a catheter. The determined data were evaluated according to standard methods. Given are the means and the standard deviations (M±SEM) of the starting values and of the maximal changes of the individual parameters (=maximal effects).

The following results were obtained:

Compound of example 88 (dosage 10 mg/kg i.d.)

| Parameter | starting value | maximal alteration | duration of action (min) |
|---|---|---|---|
| BP(s) (mm Hg) | 123 ± 26 | −23 ± 6 | >180 |
| BP(d) (mm Hg) | 83 ± 24 | −20 ± 8 | >180 |
| LVEDP (mm Hg) | 4 ± 0.6 | −1.3 ± 0.3 | >180 |
| $dP/dt_{max}$ (mm Hg/sec)) | 1800 ± 289 | −633 ± 33 | >180 |
| HR (beats/min) | 98 ± 2 | −8 ± 2 | >180 |

The invention may be embodied in other specific forms and those skilled in the art will recognize that various changes and modifications can be made without departing from the spirit or essential characteristics thereof. The present embodiment is, therefore, considered in all respects as illustrative and not restrictive, the scope of the appended claims rather than by the foregoing description, and all changes which come within the meaning and range of equivalency of the claims are therefore intended to be embraced therein.

We claim:

1. A compound of formula I, a stereoisomeric form thereof, or a physiologically acceptable salt thereof:

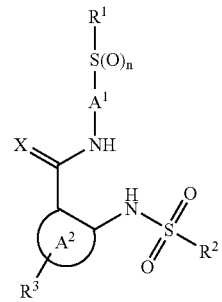

I wherein $A^1$ is a divalent heteroarylene residue, and is unsubstituted or substituted by one or more identical or different substituents chosen from halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, —NH—CHO, —NH—CO—$(C_1-C_5)$-alkyl, —CN, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl, CHO, —CO—$(C_1-C_5)$-alkyl, —S(O)$_n$—$(C_1-C_4)$-alkyl, —S(O)$_n$-phenyl, and —S(O)$_n$-tolyl;

$A^2$, which comprises the two carbon atoms bonded to the groups C(=X)—NH— and NH—SO$_2$R$^2$, is a benzene ring or a naphthalene ring;

$R^1$, when n in the group $R^1$—S(O)$_n$— is 0, is aryl, heterocyclyl, or $(C_1-C_{18})$-alkyl which is unsubstituted or substituted by one or more identical or different residues $R^4$, or is —CN, or when n in the group $R^1$—S(O)$_n$— is 1, $R^1$ is aryl, heterocyclyl, or $(C_1-C_{18})$-alkyl which is unsubstituted or substituted by one or more identical or different residues $R^4$, or when n in the group $R^1$—S(O)$_n$— is 2, $R^1$ is aryl, heterocyclyl, or $(C_1-C_{18})$-alkyl which is unsubstituted or substituted by one or more identical or different residues $R^4$, or $R^1$ is $NR^5R^6$;

$R^2$ is aryl, heterocyclyl, $NR^5R^6$, or $(C_1-C_{10})$-alkyl which is unsubstituted or substituted by one or more identical or different residues $R^4$;

$R^3$ is one or more identical or different residues chosen from hydrogen, halogen, $CF_3$, OH, —O—$(C_1-C_7)$-alkyl, —O—$(C_2-C_4)$-alkyl-O—$(C_1-C_7)$-alkyl, —O-aryl, $(C_1-C_2)$-alkylenedioxy, $NO_2$, —CN, $NR^7R^8$, —CO—$NR^7R^8$, —CO—OH, —CO—O—$(C_1-C_5)$-alkyl, heterocyclyl, —S(O)$_n$—$(C_1-C_5)$-alkyl, and $(C_1-C_5)$-alkyl which is unsubstituted or substituted by one or more identical or different residues $R^4$;

$R^4$ is fluorine, OH, —O—$(C_1-C_{10})$-alkyl, —O—$(C_2-C_4)$-alkyl-O—$(C_1-C_7)$-alkyl, —O-aryl, —CN, $NR^7R^8$, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl, or oxo;

43

$R^5$ is hydrogen, $(C_1-C_{10})$-alkyl which is unsubstituted or substituted by one or more identical or different substituents chosen from $R^4$ and aryl,
or is aryl, heterocyclyl, —CO—$NR^7R^8$, —CO-aryl, or —CO—$(C_1-C_{10})$-alkyl wherein the alkyl residue is unsubstituted or substituted by one or more identical or different residues $R^4$;

$R^6$ is hydrogen, $(C_1-C_{10})$-alkyl which is unsubstituted or substituted by one or more identical or different substituents chosen from $R^4$ and aryl, or is aryl, heterocyclyl, —CO—$NR^7R^8$, —CO-aryl, or —CO—$(C_1-C_{10})$-alkyl wherein the alkyl residue is unsubstituted or substituted by one or more identical or different residues $R^4$;

or $R^5$ and $R^6$ together with the nitrogen atom to which they are bonded form a 5-membered to 8-membered saturated or partially unsaturated ring, wherein said ring optionally further comprises one or more ring heteroatoms chosen from nitrogen, oxygen, and sulfur, and wherein said ring is unsubstituted or substituted by one or more identical or different substituents chosen from fluorine, $(C_1-C_5)$-alkyl, hydroxy-$(C_1-C_3)$-alkyl-, —$(C_1-C_3)$-alkyl-O—$(C_1-C_4)$-alkyl, aryl, $CF_3$, OH, —O—$(C_1-C_7)$-alkyl, —O-aryl, —O—$(C_2-C_4)$-alkyl-O—$(C_1-C_7)$-alkyl, $(C_2-C_3)$-alkylenedioxy, $NR^7R^8$, —CN, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, CHO, —CO—$(C_1-C_5)$-alkyl, —S(O)$_n$—$(C_1-C_4)$-alkyl, —S(O)$_n$—$NH_2$, —S(O)$_n$—NH—$(C_1-C_3)$-alkyl, —S(O)$_n$—N$((C_1-C_3)$-alkyl$)_2$, oxo, —$(CH_2)_m$—$NH_2$, —$(CH_2)_m$—NH—$(C_1-C_4)$-alkyl, and —$(CH_2)_m$—N$((C_1-C_4)$-alkyl$)_2$ where in the substituent —$(CH_2)_m$—N$((C_1-C_4)$-alkyl$)_2$ the two alkyl groups are independent, identical or different, or are connected by a single bond and together with the nitrogen atom to which they are bonded form a 5-membered to 7-membered ring, which optionally further comprises an oxygen atom, sulfur atom, or a group $NR^5$ as a ring member;

$R^7$ is hydrogen or $(C_1-C_7)$-alkyl which is unsubstituted or substituted by one or more identical or different substituents chosen from OH, —O—$(C_1-C_5)$-alkyl, $NH_2$, —NH—$(C_1-C_4)$-alkyl, and —N$((C_1-C_4)$-alkyl$)_2$ where in the substituent N$((C_1-C_4)$-alkyl$)_2$ the two alkyl groups are independent, identical or different, or are connected by a single bond and together with the nitrogen atom to which they are bonded form a 5-membered to 7-membered ring, wherein said ring optionally further comprises an oxygen atom, sulfur atom, or a group $NR^5$ as a ring member;

$R^8$ is hydrogen, —CO—$(C_1-C_4)$-alkyl, or $(C_1-C_7)$-alkyl which is unsubstituted or substituted by one or more identical or different substituents chosen from OH, —O—$(C_1-C_5)$-alkyl, $NH_2$, —NH—$(C_1-C_4)$-alkyl, and —N$((C_1-C_4)$-alkyl$)_2$ where in the substituent N$((C_1-C_4)$-alkyl$)_2$ the two alkyl groups are independent, identical or different, or are connected by a single bond and together with the nitrogen atom to which they are bonded form a 5-membered to 7-membered ring which optionally further comprises an oxygen atom, a sulfur atom, or a group $NR^5$ as ring member;

aryl is phenyl, naphthyl, or heteroaryl, and is unsubstituted or substituted by one or more identical or different substituents chosen from halogen, $(C_1-C_5)$-

44 alkyl, phenyl, tolyl, $CF_3$, —O—$CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, —NH—CHO, —NH—CO—$(C_1-C_5)$-alkyl, —CN, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl, CHO, —CO—$(C_1-C_5)$-alkyl, —S(O)$_n$—$(C_1-C_4)$-alkyl, —S(O)$_n$-phenyl, and —S(O)$_n$-tolyl;

heteroaryl and heteroarylene, independently of each other, are a residue of a monocyclic 5-membered or 6-membered aromatic heterocycle or of a bicyclic 8-membered to 10-membered aromatic heterocycle, wherein said heterocycles comprise one or more ring heteroatoms chosen from nitrogen, oxygen, and sulfur;

heterocyclyl is a residue of a monocyclic or polycyclic 5-membered to 11-membered saturated or partially unsaturated heterocycle which comprises one or more ring heteroatoms chosen from nitrogen, oxygen, and sulfur, and which is unsubstituted or substituted by one or more identical or different substituents chosen from fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, —CN, —CO—$NH_2$, —CO—NH—$(C_1-C_3)$-alkyl, —CO—N$((C_1-C_3)$-alkyl$)_2$, —CO—OH, and —CO—O—$(C_1-C_5)$-alkyl;

n is 0, 1, or 2;

m is 2, 3, or 4; and

X is oxygen or NH, or X is a nitrogen atom which via a single bond is attached to a ring carbon atom in the group $A^1$ which ring carbon atom is directly adjacent to the carbon atom in $A^1$ bonded to the group —NH—C(═X)— so that the group —NH—C(═X)— together with the carbon atoms in $A^1$ bonded to it forms an anellated imidazole ring.

2. The compound of the formula I as claimed in claim 1, wherein $A^1$ is a 5-membered or 6-membered heteroarylene residue, wherein said residue is unsubstituted or substituted as set forth in claim 1.

3. The compound of the formula I as claimed in claim 1, wherein X is oxygen.

4. The compound of the formula I as claimed in claim 1, wherein $R^2$ is aryl and is unsubstituted or substituted as set forth in claim 1.

5. The compound of the formula I as claimed in claim 1, wherein $R^1$ is $(C_1-C_7)$-alkyl, aryl, or $NR^5R^6$, and is unsubstituted or substituted as set forth in claim 1.

6. The compound of the formula I as claimed in claim 1, wherein $R^1$ is $NR^5R^6$ and $R^5$ and $R^6$ independently of one another are hydrogen, $(C_1-C_9)$-alkyl, $(C_1-C_4)$-alkyl-O—$(C_1-C_3)$-alkyl-, or 5-membered or 6-membered aryl or $R^5$ and $R^6$ together with the nitrogen atom to which they are bonded form a 5-membered to 7-membered heterocycle which optionally further comprises an additional ring heteroatom chosen from nitrogen, oxygen, and sulfur, wherein said heterocycle is unsubstituted or substituted by one or more identical or different residues chosen from $(C_1-C_3)$-alkyl, hydroxy-$(C_1-C_3)$-alkyl-, 5-membered or 6-membered aryl, carbamoyl, hydroxy, and oxo.

7. The compound of the formula I as claimed in claim 1, wherein $A^1$ is phenylene or heteroarylene, and is unsubstituted or substituted by one or more identical or different substituents chosen from halogen, $(C_1-C_4)$-alkyl, $CF_3$, —O—$(C_1-C_4)$-alkyl, and —CN;

$A^2$ is a benzene ring or a napthalene ring;

$R^1$, when n in the group $R^1$—S(O)$_n$— is 1, is $(C_1-C_7)$-alkyl which is unsubstituted or substituted by one or more identical or different residues $R^4$, or $R^1$ is aryl, or when n in the group $R^1$—S(O)$_n$— is 2, $R^1$ is aryl, or $(C_1-C_7)$-alkyl which is unsubstituted or substituted by one or more identical or different residues $R^4$, or $R^1$ is $NR^5R^6$;

$R^2$ is aryl;

$R^3$ is one or more identical or different residues chosen from hydrogen, halogen, $CF_3$, OH, —O—$(C_1-C_4)$-alkyl, —O—$(C_2-C_4)$-alkyl-O—$(C_1-C_4)$-alkyl, —O-aryl, $NO_2$, —CN, $NR^7R^8$, —CO—$NR^7R^8$, —CO—OH, —CO—O—$(C_1-C_4)$-alkyl, heterocyclyl, —S(O)$_n$—$(C_1-C_4)$-alkyl, and $(C_1-C_4)$-alkyl which is unsubstituted or substituted by one or more identical or different residues $R^4$;

$R^4$ is fluorine, OH, —O—$(C_1-C_{10})$alkyl, —O—$(C_2-C_4)$-alkyl-O—$(C_1-C_7)$-alkyl, —O-aryl, —CN, $NR^7R^8$, —CO—$NH_2$, —CO—NH—$(C_1-C_3)$-alkyl, —CO—$N((C_1-C_3)$-alkyl)$_2$, —CO—OH, —CO—O—$(C_1C_4)$-alkyl, heterocyclyl, or oxo;

$R^5$ and $R^6$ independently of one another are hydrogen, $(C_1-C_9)$-alkyl, $(C_1-C_4)$-alkyl-O—$(C_1-C_3)$-alkyl-, or aryl, or $R^5$ and $R^6$ together with the nitrogen to which they are bonded form a 5-membered, 6-membered, or 7-membered heterocycle, wherein said heterocycle optionally further comprises an additional ring heteroatom chosen from nitrogen, oxygen, and sulfur, and wherein said heterocycle is unsubstituted or substituted by one or more identical or different residues chosen from $(C_1-C_3)$-alkyl, hydroxy-$(C_1-C_3)$-alkyl-, aryl, carbamoyl, hydroxy, and oxo;

$R^7$ is hydrogen, $(C_1-C_3)$-alkyl, $((C_1-C_4)$-alkyl)$_2$N—$(C_1-C_3)$-alkyl-, or $(C_1-C_4)$-alkyl-O—$(C_1-C_3)$-alkyl-;

$R^8$ is hydrogen, $(C_1-C_3)$-alkyl, or acetyl;

aryl is phenyl or heteroaryl, and is unsubstituted or substituted by one or more identical or different substituents chosen from halogen, $(C_1-C_4)$-alkyl, phenyl, $CF_3$, $NO_2$, —O—$(C_1-C_4)$-alkyl, $(C_1-C_2)$-alkylenedioxy, $NH_2$, —NH—CO—$(C_1-C_4)$-alkyl, —CN, —CO—$NH_2$, —CO—OH, and —CO—O—$(C_1-C_4)$-alkyl;

heteroaryl and heteroarylene are a residue of a monocyclic 5-membered or 6-membered aromatic heterocycle which comprises one or more identical or different ring heteroatoms chosen from nitrogen, oxygen, and sulfur;

heterocyclyl is a residue of a monocyclic 5-membered or 6-membered saturated heterocycle which comprises one or more identical or different ring heteroatoms chosen from nitrogen, oxygen, and sulfur, and which is unsubstituted or substituted by one or more identical or different substituents chosen from fluorine, $(C_1-C_4)$-alkyl, OH, —O—$(C_1-C_4)$-alkyl, $NH_2$, —CN, —CO—$NH_2$, —CO—OH, and —CO—O—$(C_1-C_4)$-alkyl;

n is 0, 1, or 2; and

X is oxygen.

8. A method for preparing a compound of formula I, comprising:

converting a cyclic aminocarboxylic acid compound of formula II into a sulfonylaminocarboxylic acid compound of formula III; and converting the sulfonylaminocarboxylic acid compound of formula III into a compound of formula I:

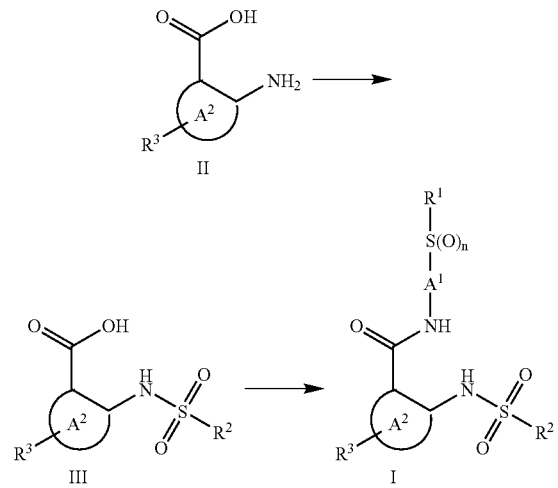

wherein, in the compounds of formulae I, II, and III:

$A^1$ is a divalent heteroarylene residue, and is unsubstituted or substituted by one or more identical or different substituents chosen from halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N($(C_1-C_3)$-alkyl)$_2$, —NH—CHO, —NH—CO—$(C_1-C_5)$-alkyl, —CN, —CO—$NH_2$, —CO—NH—$(C_1-C_3)$-alkyl, —CO—N($(C_1-C_3)$-alkyl)$_2$, —CO—OH, —CO—O—$(C_1-C_5)$-alkyl, heterocyclyl, CHO, —CO—$(C_1-C_5)$-alkyl, —S(O)$_n$—$(C_1-C_4)$-alkyl, —S(O)$_n$-phenyl, and —S(O)$_n$-tolyl;

$A^2$, which comprises the two carbon atoms bonded to the groups C(=X)—NH— and NH—$SO_2R^2$, is a benzene ring or a naphthalene ring;

$R^1$, when n in the group $R^1$—S(O)$_n$— is 0, is aryl, heterocyclyl, or $(C_1-C_{18})$-alkyl which is unsubstituted or substituted by one or more identical or different residues $R^4$, or is —CN, or when n in the group $R^1$—S(O)$_n$— is 1, $R^1$ is aryl, heterocyclyl, or $(C_1-C_{18})$-alkyl which is unsubstituted or substituted by one or more identical or different residues $R^4$, or when n in the group $R^1$—S(O)$_n$— is 2, $R^6$ is aryl, heterocyclyl, or $(C_1-C_{18})$-alkyl which is unsubstituted or substituted by one or more identical or different residues $R^4$, or $R^1$ is $NR^5R^6$;

$R^2$ is aryl, heterocyclyl, $NR^5R^6$, or $(C_1-C_{10})$-alkyl which is unsubstituted or substituted by one or more identical or different residues $R^4$;

$R^3$ is one or more identical or different residues chosen from hydrogen, halogen, $CF_3$, OH, —O—$(C_1-C_7)$-alkyl, —O—$(C_2-C_4)$-alkyl-O—$(C_1-C_7)$-alkyl, —O-aryl, $(C_1-C_2)$-alkylenedioxy, $NO_2$, —CN, $NR^7R^8$, —CO—$NR^7R^8$, —CO—OH, —CO—O—$(C_1-C_5)$-alkyl, heterocyclyl, —S(O)$_n$—$(C_1-C_5)$-alkyl, and $(C_1-C_5)$-alkyl which is unsubstituted or substituted by one or more identical or different residues $R^4$;

$R^4$ is fluorine, OH, —O—$(C_1$-$C_{10})$-alkyl, —O—$(C_2$-$C_4)$-alkyl-O—$(C_1$-$C_7)$-alkyl, —O-aryl, —CN, $NR^7R^8$, —CO—$NH_2$, —CO—NH—$(C_1$-$C_3)$-alkyl, —CO—N$((C_1$-$C_3)$-alkyl$)_2$, —CO—OH, —CO—O—$(C_1$-$C_5)$-alkyl, heterocyclyl, or oxo;

$R^5$ is hydrogen, $(C_1$-$C_{10})$-alkyl which is unsubstituted or substituted by one or more identical or different substituents chosen from $R^4$ and aryl, or is aryl, heterocyclyl, —CO—$NR^7R^8$, —CO-aryl, or —CO—$(C_1$-$C_{10})$-alkyl wherein the alkyl residue is unsubstituted or substituted by one or more identical or different residues $R^4$;

$R^6$ is hydrogen, $(C_1$-$C_{10})$-alkyl which is unsubstituted or substituted by one or more identical or different substituents chosen from $R^4$ and aryl, or is aryl, heterocyclyl, —CO—$NR^7R^8$, —CO-aryl, or —CO—$(C_1$-$C_{10})$-alkyl wherein the alkyl residue is unsubstituted or substituted by one or more identical or different residues $R^4$;

or $R^5$ and $R^6$ together with the nitrogen atom to which they are bonded form a 5-membered to 8-membered saturated or partially unsaturated ring, wherein said ring optionally further comprises one or more ring heteroatoms chosen from nitrogen, oxygen, and sulfur, and wherein said ring is unsubstituted or substituted by one or more identical or different substituents chosen from fluorine, $(C_1$-$C_5)$-alkyl, hydroxy-$(C_1$-$C_3)$-alkyl-, —$(C_1$-$C_3)$-alkyl-O—$(C_{1-4})$-alkyl, aryl, $CF_3$, OH, —O—$(C_1$-$C_7)$-alkyl, —O-aryl, —O—$(C_2$-$C_4)$-alkyl-O—$(C_1$-$C_7)$-alkyl, $(C_2$-$C_3)$-alkylenedioxy, $NR^7R^8$, —CN, —CO—$NH_2$, —CO—NH—$(C_1$-$C_3)$-alkyl, —CO—N$((C_1$-$C_3)$-alkyl$)_2$, —CO—OH, —CO—O—$(C_1$-$C_5)$-alkyl, CHO, —CO—$(C_1$-$C_5)$-alkyl, —S(O)$_n$—$(C_1$-$C_4)$-alkyl, —S(O)$_n$—$NH_2$, —S(O)$_n$—NH—$(C_1$-$C_3)$-alkyl, —S(O)$_n$—N$((C_1$-$C_3)$-alkyl$)_2$, oxo, —$(CH_2)_m$—$NH_2$, —$(CH_2)_m$—NH—$(C_1$-$C_4)$-alkyl, and —$(CH_2)_m$—N$((C_1$-$C_4)$-alkyl$)_2$ where in the substituent —$(CH_2)_m$—N$((C_1$-$C_4)$-alkyl$)_2$ the two alkyl groups are independent, identical or different, or are connected by a single bond and together with the nitrogen atom to which they are bonded form a 5-membered to 7-membered ring, which optionally further comprises an oxygen atom, sulfur atom, or a group $NR^5$ as a ring member;

$R^7$ is hydrogen or $(C_1$-$C_7)$-alkyl which is unsubstituted or substituted by one or more identical or different substituents chosen from OH, —O—$(C_1$-$C_5)$-alkyl, $NH_2$, —NH—$(C_1$-$C_4)$-alkyl, and —N$((C_1$-$C_4)$-alkyl$)_2$ where in the substituent N$((C_1$-$C_4)$-alkyl$)_2$ the two alkyl groups are independent, identical or different, or are connected by a single bond and together with the nitrogen atom to which they are bonded form a 5-membered to 7-membered ring, wherein said ring optionally further comprises an oxygen atom, sulfur atom, or a group $NR^5$ as a ring member;

$R^8$ is hydrogen, —CO—$(C_1$-$C_4)$-alkyl, or $(C_1$-$C_7)$-alkyl which is unsubstituted or substituted by one or more identical or different substituents chosen from OH, —O—$(C_1$-$C_5)$-alkyl, $NH_2$, —NH—$(C_1$-$C_4)$-alkyl, and —N$((C_1$-$C_4)$-alkyl$)_2$ where in the substituent N$((C_1$-$C_4)$-alkyl$)_2$ the two alkyl groups are independent, identical or different, or are connected by a single bond and together with the nitrogen atom to which they are bonded form a 5-membered to 7-membered ring which optionally further comprises an oxygen atom, a sulfur atom, or a group $NR^5$ as ring member;

aryl is phenyl, naphthyl, or heteroaryl, and is unsubstituted or substituted by one or more identical or different substituents chosen from halogen, $(C_1$-$C_5)$-alkyl, phenyl, tolyl, $CF_3$, —O—$CF_3$, $NO_2$, OH, —O—$(C_1$-$C_5)$-alkyl, —O—$(C_2$-$C_4)$-alkyl-O—$(C_1$-$C_3)$-alkyl, $(C_1$-$C_2)$-alkylenedioxy, $NH_2$, —NH—$(C_1$-$C_3)$-alkyl, —N$((C_1$-$C_3)$-alkyl$)_2$, —NH—CHO, —NH—CO—$(C_1$-$C_5)$-alkyl, —CN, —CO—$NH_2$, —CO—NH—$(C_1$-$C_3)$-alkyl, —CO—N$((C_1$-$C_3)$-alkyl$)_2$, —CO—OH, —CO—O—$(C_1$-$C_5)$-alkyl, heterocyclyl, CHO, —CO—$(C_1$-$C_5)$-alkyl, —S(O)$_n$—$(C_1$-$C_4)$-alkyl, —S(O)$_n$-phenyl, and —S(O)$_n$-tolyl;

heteroaryl and heteroarylene, independently of each other, are a residue of a monocyclic 5-membered or 6-membered aromatic heterocycle or of a bicyclic 8-membered to 10-membered aromatic heterocycle, wherein said heterocycles comprise one or more ring heteroatoms chosen from nitrogen, oxygen, and sulfur;

heterocyclyl is a residue of a monocyclic or polycyclic 5-membered to 11-membered saturated or partially unsaturated heterocycle which comprises one or more ring heteroatoms chosen from nitrogen, oxygen, and sulfur, and which is unsubstituted or substituted by one or more identical or different substituents chosen from fluorine, $(C_1$-$C_5)$-alkyl, OH, —O—$(C_1$-$C_5)$-alkyl, —O—$(C_2$-$C_4)$-alkyl-O—$(C_1$-$C_3)$-alkyl, $NH_2$, —NH—$(C_1$-$C_3)$-alkyl, —N$((C_1$-$C_3)$-alkyl$)_2$, —CN, —CO—$NH_2$, —CO—NH—$(C_1$-$C_3)$-alkyl, —CO—N$((C_1$-$C_3)$-alkyl$)_2$, —CO—OH, and —CO—O—$(C_1$-$C_5)$-alkyl;

n is 0, 1, or 2;

m is 2, 3, or 4; and

X is oxygen or NH, or X is a nitrogen atom which via a single bond is attached to a ring carbon atom in the group $A^1$ which ring carbon atom is directly adjacent to the carbon atom in $A^1$ bonded to the group —NH—C(=X)— so that the group —NH—C(=X)— together with the carbon atoms in $A^1$ bonded to it forms an anellated imidazole ring;

or when one or more of said residues, independent of each other, are present in protected form or in a form of precursor groups.

9. A method for preparing a compound of formula I, comprising:

converting a cyclic nitrocarboxylic acid compound of formula IX into a nitrocarboxamide compound of formula XII; and converting the nitrocarboxamide compound of the formula XII into a compound of formula I by reducing the nitro group to an amino group, and sulfonylating the amino group:

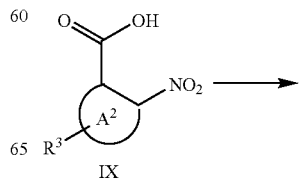

IX

-continued

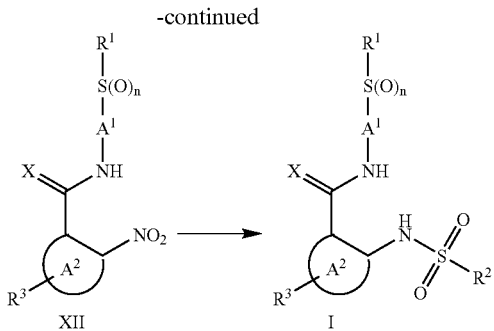

wherein, in the compounds of formulae IX, XII, and I:

$A^1$ is a divalent heteroarylene residue, and is unsubstituted or substituted by one or more identical or different substituents chosen from halogen, $(C_1\text{-}C_5)$-alkyl, phenyl, tolyl, $CF_3$, $NO_2$, OH, —O—$(C_1\text{-}C_5)$-alkyl, —O—$(C_2\text{-}C_4)$-alkyl-O—$(C_1\text{-}C_3)$-alkyl, $(C_1\text{-}C_2)$-alkylenedioxy, $NH_2$, —NH—$(C_1\text{-}C_3)$-alkyl, —N($(C_1\text{-}C_3)$-alkyl)$_2$, —NH—CHO, —NH—CO—$(C_1\text{-}C_5)$-alkyl, —CN, —CO—$NH_2$, —CO—NH—$(C_1\text{-}C_3)$-alkyl, —CO—N($(C_1\text{-}C_3)$-alkyl)$_2$, —CO—OH, —CO—O—$(C_1\text{-}C_5)$-alkyl, heterocyclyl, CHO, —CO—$(C_1\text{-}C_5)$-alkyl, —S(O)$_n$—$(C_1\text{-}C_4)$-alkyl, —S(O)$_n$-phenyl, and —S(O)$_n$-tolyl;

$A^2$, which comprises the two carbon atoms bonded to the groups C(=X)—NH— and NH—$SO_2R^2$, is a benzene ring or a naphthalene ring;

$R^1$, when n in the group $R^1$—S(O)$_n$— is 0, is aryl, heterocyclyl, or $(C_1\text{-}C_{18})$-alkyl which
is unsubstituted or substituted by one or more identical or different residues $R^4$, or is —CN, or
when n in the group $R^1$—S(O)$_n$— is 1, $R^1$ is aryl, heterocyclyl, or $(C_1\text{-}C_{18})$-alkyl which is unsubstituted or substituted by one or more identical or different residues $R^4$, or
when n in the group $R^1$—S(O)$_n$— is 2, $R^1$ is aryl, heterocyclyl, or $(C_1\text{-}C_{18})$-alkyl which is unsubstituted or substituted by one or more identical or different residues $R^4$, or $R^1$ is $NR^5R^6$;

$R^2$ is aryl, heterocyclyl, $NR^5R^6$, or $(C_1\text{-}C_{10})$-alkyl which is unsubstituted or substituted by one or more identical or different residues $R^4$;

$R^3$ is one or more identical or different residues chosen from hydrogen, halogen, $CF_3$, OH, —O—$(C_1\text{-}C_7)$-alkyl, —O—$(C_2\text{-}C_4)$-alkyl-O—$(C_1\text{-}C_7)$-alkyl, —O-aryl, $(C_1\text{-}C_2)$-alkylenedioxy, $NO_2$, —CN, $NR^7R^8$, —CO—$NR^7R^8$, —CO—OH, —CO—O—$(C_1\text{-}C_5)$-alkyl, heterocyclyl, —S(O)$_n$—$(C_1\text{-}C_5)$-alkyl, and $(C_1\text{-}C_5)$-alkyl
which is unsubstituted or substituted by one or more identical or different residues $R^4$;

$R^4$ is fluorine, OH, —O—$(C_1\text{-}C_{10})$-alkyl, —O—$(C_2\text{-}C_4)$-alkyl-O—$(C_1\text{-}C_7)$-alkyl, —O-aryl, —CN, $NR^7R^8$, —CO—$NH_2$, —CO—NH—$(C_1\text{-}C_3)$-alkyl, —CO—N($(C_1\text{-}C_3)$-alkyl)$_2$, —CO—OH, —CO—O—$(C_1\text{-}C_5)$-alkyl, heterocyclyl, or oxo;

$R^5$ is hydrogen, $(C_1\text{-}C_{10})$-alkyl which is unsubstituted or substituted by one or more identical or different substituents chosen from $R^4$ and aryl,
or is aryl, heterocyclyl, —CO—$NR^7R^8$, —CO-aryl, or —CO—$(C_1\text{-}C_{10})$-alkyl wherein the alkyl residue is unsubstituted or substituted by one or more identical or different residues $R^4$;

$R^6$ is hydrogen, $(C_1\text{-}C_{10})$-alkyl which is unsubstituted or substituted by one or more identical or different substituents chosen from $R^4$ and aryl,
or is aryl, heterocyclyl, —CO—$NR^7R^8$, —CO-aryl, or —CO—$(C_1\text{-}C_{10})$-alkyl wherein the alkyl residue is unsubstituted or substituted by one or more identical or different residues $R^4$;

or $R^5$ and $R^6$ together with the nitrogen atom to which they are bonded form a 5-membered to 8-membered saturated or partially unsaturated ring,
wherein said ring optionally further comprises one or more ring heteroatoms chosen from nitrogen, oxygen, and sulfur, and
wherein said ring is unsubstituted or substituted by one or more identical or different substituents chosen from fluorine, $(C_1\text{-}C_5)$-alkyl, hydroxy-$(C_1\text{-}C_3)$-alkyl-, —$(C_1\text{-}C_3)$-alkyl-O—$(C_1\text{-}C_4)$-alkyl, aryl, $CF_3$, OH, —O—$(C_1\text{-}C_7)$-alkyl, —O-aryl, —O—$(C_2\text{-}C_4)$-alkyl-O—$(C_1\text{-}C_7)$-alkyl, $(C_2\text{-}C_3)$-alkylenedioxy, $NR^7R^8$, —CN, —CO—$NH_2$, —CO—NH—$(C_1\text{-}C_3)$-alkyl, —CO—N($(C_1\text{-}C_3)$-alkyl)$_2$, —CO—OH, —CO—O—$(C_1\text{-}C_5)$-alkyl, CHO, —CO—$(C_1\text{-}C_5)$-alkyl, —S(O)$_n$—$(C_1\text{-}C_4)$-alkyl, —S(O)$_n$—$NH_2$, —S(O)$_n$—NH—$(C_1\text{-}C_3)$-alkyl, —S(O)$_n$—N($(C_1\text{-}C_3)$-alkyl)$_2$, oxo, —$(CH_2)_m$—$NH_2$, —$(CH_2)_m$—NH—$(C_1\text{-}C_4)$-alkyl, and —$(CH_2)_m$—N($(C_1\text{-}C_4)$-alkyl)$_2$ where in the substituent —$(CH_2)_m$—N($(C_1\text{-}C_4)$-alkyl)$_2$ the two alkyl groups are independent, identical or different, or are connected by a single bond and together with the nitrogen atom to which they are bonded form a 5-membered to 7-membered ring, which optionally further comprises an oxygen atom, sulfur atom, or a group $NR^5$ as a ring member;

$R^7$ is hydrogen or $(C_1\text{-}C_7)$-alkyl which is unsubstituted or substituted by one or more identical or different substituents chosen from OH, —O—$(C_1\text{-}C_5)$-alkyl, $NH_2$, —NH—$(C_1\text{-}C_4)$-alkyl, and —N($(C_1\text{-}C_4)$-alkyl)$_2$ where in the substituent N($(C_1\text{-}C_4)$-alkyl)$_2$ the two alkyl groups are independent, identical or different, or are connected by a single bond and together with the nitrogen atom to which they are bonded form a 5-membered to 7-membered ring, wherein said ring optionally further comprises an oxygen atom, sulfur atom, or a group $NR^5$ as a ring member;

$R^8$ is hydrogen, —CO—$(C_1\text{-}C_4)$-alkyl, or $(C_1\text{-}C_7)$-alkyl which is unsubstituted or substituted by one or more identical or different substituents chosen from OH, —O—$(C_1\text{-}C_5)$-alkyl, $NH_2$, —NH—$(C_1\text{-}C_4)$-alkyl, and —N($(C_1\text{-}C_4)$-alkyl)$_2$ where in the substituent N($(C_1\text{-}C_4)$-alkyl)$_2$ the two alkyl groups are independent, identical or different, or are connected by a single bond and together with the nitrogen atom to which they are bonded form a 5-membered to 7-membered ring which optionally further comprises an oxygen atom, a sulfur atom, or a group $NR^5$ as ring member;

aryl is phenyl, naphthyl, or heteroaryl, and is unsubstituted or substituted by one or more identical or different substituents chosen from halogen, $(C_1\text{-}C_5)$-alkyl, phenyl, tolyl, $CF_3$, —O—$CF_3$, $NO_2$, OH, —O—$(C_1\text{-}C_5)$-alkyl, —O—$(C_2\text{-}C_4)$-alkyl-O—$(C_1\text{-}C_3)$-alkyl, $(C_1\text{-}C_2)$-alkylenedioxy, $NH_2$, —NH—$(C_1\text{-}C_3)$-alkyl, —N($(C_1\text{-}C_3)$-alkyl)$_2$, —NH—CHO, —NH—CO—$(C_1\text{-}C_5)$-alkyl, —CN, —CO—$NH_2$, —CO—NH—$(C_1\text{-}C_3)$-alkyl, —CO—N($(C_1\text{-}C_3)$-alkyl)$_2$, —CO—OH, —CO—O—$(C_1\text{-}C_5)$-alkyl, heterocyclyl, CHO, —CO—$(C_1\text{-}C_5)$-alkyl, —S(O)$_n$—$(C_1\text{-}C_4)$-alkyl, —S(O)$_n$-phenyl, and —S(O)$_n$-tolyl;

heteroaryl and heteroarylene, independently of each other, are a residue of a monocyclic 5-membered or 6-membered aromatic heterocycle or of a bicyclic 8-membered to 10-membered aromatic heterocycle, wherein said heterocycles comprise one or more ring heteroatoms chosen from nitrogen, oxygen, and sulfur;

heterocyclyl is a residue of a monocyclic or polycyclic 5-membered to 11-membered saturated or partially unsaturated heterocycle which comprises one or more ring heteroatoms chosen from nitrogen, oxygen, and sulfur, and which is unsubstituted or substituted by one or more identical or different substituents chosen from fluorine, $(C_1-C_5)$-alkyl, OH, —O—$(C_1-C_5)$-alkyl, —O—$(C_2-C_4)$-alkyl-O—$(C_1-C_3)$-alkyl, $NH_2$, —NH—$(C_1-C_3)$-alkyl, —N$((C_1-C_3)$-alkyl$)_2$, —CN, —CO—$NH_2$, —CO—NH—$(C_1-C_3)$-alkyl, —CO—N$((C_1-C_3)$-alkyl$)_2$, —CO—OH, and —CO—O—$(C_1-C_5)$-alkyl;

n is 0, 1, or 2;

m is 2, 3, or 4; and

X is oxygen or NH, or X is a nitrogen atom which via a single bond is attached to a ring carbon atom in the group $A^1$ which ring carbon atom is directly adjacent to the carbon atom in $A^1$ bonded to the group —NH—C(=X)— so that the group —NH—C(=X)— together with the carbon atoms in $A^1$ bonded to it forms an anellated imidazole ring;

or when one or more of said residues, independent of each other, are present in protected form or in a form of precursor groups.

10. A composition, comprising a compound of formula I:

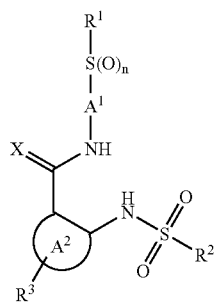

I wherein $A^1$ is a divalent heteroarylene residue, and is unsubstituted or substituted by one or more identical or different substituents chosen from halogen, $(C_1-C_5)$-alkyl, phenyl, tolyl, $CF_3$, $NO_2$, OH, —O—$(C_1-C_5)$-alkyl, —O—$(C_2-C_4)$-alkyl-O—$(C_1-C_3)$-alkyl, $(C_1-C_2)$-alkylenedioxy, $NH_2$, —NH—$(C_1-C_3)$-alkyl, —N$((C_1-C_3)$-alkyl$)_2$, —NH—CHO, —NH—CO—$(C_1-C_5)$-alkyl, —CN, —CO—$NH_2$, —CO—NH—$(C_1-C_3)$-alkyl, —CO—N$((C_1-C_3$alkyl$)_2$, —CO—OH, —CO—O—$(C_1-C_5)$-alkyl, heterocyclyl, CHO, —CO—$(C_1-C_5)$-alkyl, —S(O)$_n$—$(C_1-C_4)$-alkyl, —S(O)$_n$-phenyl, and —S(O)$_n$-tolyl;

$A^2$, which comprises the two carbon atoms bonded to the groups C(=X)—NH— and NH—SO$_2$R$^2$, is a benzene ring or a naphthalene ring;

$R^1$, when n in the group $R^1$—S(O)$_n$— is 0, is aryl, heterocyclyl, or $(C_1-C_{18})$-alkyl which is unsubstituted or substituted by one or more identical or different residues $R^4$, or is —CN, or when n in the group $R^1$—S(O)$_n$— is 1, $R^1$ is aryl, heterocyclyl, or $(C_1-C_{18})$-alkyl which is unsubstituted or substituted by one or more identical or different residues $R^4$, or when n in the group $R^1$—S(O)$_n$— is 2, $R^1$ is aryl, heterocyclyl, or $(C_1-C_{18})$-alkyl which is unsubstituted or substituted by one or more identical or different residues $R^4$, or $R^1$ is $NR^5R^6$;

$R^2$ is aryl, heterocyclyl, $NR^5R^6$, or $(C_1-C_{10})$-alkyl which is unsubstituted or substituted by one or more identical or different residues $R^4$;

$R^3$ is one or more identical or different residues chosen from hydrogen, halogen, $CF_3$, OH, —O—$(C_1-C_7)$-alkyl, —O—$(C_2-C_4)$-alkyl-O—$(C_1-C_7)$-alkyl, —O-aryl, $(C_1-C_2)$-alkylenedioxy, $NO_2$, —CN, $NR^7R^8$, —CO—$NR^7R^8$, —CO—OH, —CO—O—$(C_1-C_5)$-alkyl, heterocyclyl, —S(O)$_n$—$(C_1-C_5)$-alkyl, and $(C_1-C_5)$-alkyl which is unsubstituted or substituted by one or more identical or different residues $R^4$;

$R^4$ is fluorine, OH, —O—$(C_1-C_{10})$-alkyl, —O—$(C_2-C_4)$-alkyl-O—$(C_1-C_7)$-alkyl, —O-aryl, —CN, $NR^7R^8$, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, heterocyclyl, or oxo;

$R^5$ is hydrogen, $(C_1-C_{10})$-alkyl which is unsubstituted or substituted by one or more identical or different substituents chosen from $R^4$ and aryl, or is aryl, heterocyclyl, —CO—$NR^7R^8$, —CO-aryl, or —CO—$(C_1-C_{10})$-alkyl wherein the alkyl residue is unsubstituted or substituted by one or more identical or different residues $R^4$;

$R^6$ is hydrogen, $(C_1-C_{10})$-alkyl which is unsubstituted or substituted by one or more identical or different substituents chosen from $R^4$ and aryl, or is aryl, heterocyclyl, —CO—$NR^7R^8$, —CO-aryl, or —CO—$(C_1-C_{10})$-alkyl wherein the alkyl residue is unsubstituted or substituted by one or more identical or different residues $R^4$;

or $R^5$ and $R^1$ together with the nitrogen atom to which they are bonded form a 5-membered to 8-membered saturated or partially unsaturated ring, wherein said ring optionally further comprises one or more ring heteroatoms chosen from nitrogen, oxygen, and sulfur, and wherein said ring is unsubstituted or substituted by one or more identical or different substituents chosen from fluorine, $(C_1-C_5)$-alkyl, hydroxy-$(C_1-C_3)$-alkyl-, —$(C_1-C_3)$-alkyl-O—$(C_1-C_4)$-alkyl, aryl, $CF_3$, OH, —O—$(C_1-C_7)$-alkyl, —O-aryl, —O—$(C_2-C_4)$alkyl-O—$(C_1-C_7)$-alkyl, $(C_2-C_3)$-alkylenedioxy, $NR^7R^8$, —CN, —CO—$NH_2$, —CO—NH—$(C_1-C_3)$-alkyl, —CO—N$((C_1-C_3)$-alkyl$)_2$, —CO—OH, —CO—O—$(C_1-C_5)$-alkyl, CHO, —CO—$(C_1-C_5)$-alkyl, —S(O)$_n$—$(C_1-C_4)$-alkyl, —S(O)$_n$—$NH_2$, —S(O)$_n$—NH—$(C_1-C_3)$-alkyl, —S(O)$_n$—N$((C_1-C_3)$-alkyl$)_2$, oxo, —$(CH_2)_m$—$NH_2$, —$(CH_2)_m$—NH—$(C_1-C_4)$-alkyl, and —$(CH_2)_m$—N$((C_1-C_4)$-alkyl$)_2$ where in the substituent —$(CH_2)_m$—N$((C_1-C_4)$-alkyl$)_2$ the two alkyl groups are independent, identical or different, or are connected by a single bond and together with the nitrogen atom to which they are bonded form a 5-membered to 7-membered ring, which optionally further comprises an oxygen atom, sulfur atom, or a group $NR^5$ as a ring member;

$R^7$ is hydrogen or $(C_1-C_7)$-alkyl which is unsubstituted or substituted by one or more identical or different substituents chosen from OH, —O—$(C_1-C_5)$-alkyl, $NH_2$, —NH—$(C_1-C_4)$-alkyl, and —N$((C_1-C_4)$-alkyl$)_2$ where in the substituent N$((C_1-C_4)$-alkyl$)_2$ the two alkyl groups are independent, identical or different, or are connected by a single bond and together with the nitrogen atom to which they are bonded form a 5-membered to 7-membered ring, wherein said ring optionally further comprises an oxygen atom, sulfur atom, or a group $NR^5$ as a ring member;

$R^8$ is hydrogen, —CO—$(C_1$-$C_4)$-alkyl, or $(C_1$-$C_7)$-alkyl which is unsubstituted or substituted by one or more identical or different substituents chosen from OH, —O—$(C_1$-$C_5)$-alkyl, $NH_2$, —NH—$(C_1$-$C_4)$-alkyl, and —N($(C_1$-$C_4)$-alkyl$)_2$ where in the substituent N($(C_1$-$C_4)$-alkyl$)_2$ the two alkyl groups are independent, identical or different, or are connected by a single bond and together with the nitrogen atom to which they are bonded form a 5-membered to 7-membered ring which optionally further comprises an oxygen atom, a sulfur atom, or a group $NR^5$ as ring member;

aryl is phenyl, naphthyl, or heteroaryl, and is unsubstituted or substituted by one or more identical or different substituents chosen from halogen, $(C_1$-$C_5)$-alkyl, phenyl, tolyl, $CF_3$, —O—$CF_3$, $NO_2$, OH, —O—$(C_1$-$C_5)$-alkyl, —O—$(C_2$-$C_4)$-alkyl-O—$(C_1$-$C_3)$-alkyl, $(C_1$-$C_2)$-alkylenedioxy, $NH_2$, —NH—$(C_1$-$C_3)$-alkyl, —N($(C_1$-$C_3)$-alkyl$)_2$, —NH—CHO, —NH—CO—$(C_1$-$C_5)$-alkyl, —CN, —CO—$NH_2$, —CO—NH—$(C_1$-$C_3)$-alkyl, —CO—N($(C_1$-$C_3)$-alkyl$)_2$, —CO—OH, —CO—O—$(C_1$-$C_5)$-alkyl, heterocyclyl, CHO, —CO—$(C_1$-$C_5)$-alkyl, —S(O)$_n$—$(C_1$-$C_4)$-alkyl, —S(O)$_n$-phenyl, and —S(O)$_n$-tolyl;

heteroaryl and heteroarylene, independently of each other, are a residue of a monocyclic 5-membered or 6-membered aromatic heterocycle or of a bicyclic 8-membered to 10-membered aromatic heterocycle, wherein said heterocycles comprise one or more ring heteroatoms chosen from nitrogen, oxygen, and sulfur;

heterocyclyl is a residue of a monocyclic or polycyclic 5-membered to 11-membered saturated or partially unsaturated heterocycle which comprises one or more ring heteroatoms chosen from nitrogen, oxygen, and sulfur, and which is unsubstituted or substituted by one or more identical or different substituents chosen from fluorine, $(C_1$-$C_5)$-alkyl, OH, —O—$(C_1$-$C_5)$-alkyl, —O—$(C_2$-$C_4)$-alkyl-O—$(C_1$-$C_3)$-alkyl, $NH_2$, —NH—$(C_1$-$C_3)$-alkyl, —N($(C_1$-$C_3)$-alkyl$)_2$, —CN, —CO—$NH_2$, —CO—NH—$(C_1$-$C_3)$-alkyl, —CO—N($(C_1$-$C_3)$-alkyl$)_2$, —CO—OH, and —CO—O—$(C_1$-$C_5)$-alkyl;

n is 0, 1, or 2;

m is 2, 3, or 4; and

X is oxygen or NH, or X is a nitrogen atom which via a single bond is attached to a ring carbon atom in the group $A^1$ which ring carbon atom is directly adjacent to the carbon atom in $A^1$ bonded to the group —NH—C(=X)— so that the group —NH—C(=X)— together with the carbon atoms in $A^1$ bonded to it forms an anellated imidazole ring;

or a stereoisomer thereof, or a physiologically acceptable salt thereof, or a mixture of two or more of any of the foregoing; and at least one pharmaceutically acceptable carrier.

* * * * *

UNITED STATES PATENT AND TRADEMARK OFFICE
CERTIFICATE OF CORRECTION

PATENT NO. : 7,326,789 B2  
APPLICATION NO. : 10/816143  
DATED : February 5, 2008  
INVENTOR(S) : Ursula Schindler et al.

Page 1 of 1

It is certified that error appears in the above-identified patent and that said Letters Patent is hereby corrected as shown below:

Claim 8, column 48, line 45, "or when one or more" should read --or wherein one or more--.

Claim 9, column 51, line 25, "or when one or more" should read --or wherein one or more--.

Claim 10, column 52, line 36, "$R^5$ and $R^1$" should read --$R^5$ and $R^6$--.

Signed and Sealed this

Twenty-seventh Day of January, 2009

JOHN DOLL  
*Acting Director of the United States Patent and Trademark Office*

UNITED STATES PATENT AND TRADEMARK OFFICE
CERTIFICATE OF CORRECTION

| | |
|---|---|
| PATENT NO. | : 7,326,789 B2 |
| APPLICATION NO. | : 10/816143 |
| DATED | : February 5, 2008 |
| INVENTOR(S) | : Ursula Schindler et al. |

Page 1 of 1

It is certified that error appears in the above-identified patent and that said Letters Patent is hereby corrected as shown below:

Title Page, item 62, after Division of application No., delete "09/994,739" and insert --09/994,730--.

Signed and Sealed this

Tenth Day of February, 2009

JOHN DOLL
*Acting Director of the United States Patent and Trademark Office*